(12) United States Patent
Barkats et al.

(10) Patent No.: US 10,590,420 B2
(45) Date of Patent: Mar. 17, 2020

(54) TREATMENT OF AMYOTROPHIC LATERAL SCLEROSIS

(71) Applicants: ASSOCIATION INSTITUT DE MYOLOGIE, Paris (FR); INSTITUT NATIONAL DE LA SANTE ET DE LA RECHERCHE MEDICALE, Paris (FR); UNIVERSITE PIERRE ET MARIE CURIE (PARIS 6), Paris (FR)

(72) Inventors: Martine Barkats, Charenton le Pont (FR); Maria-Grazia Biferi, Paris (FR); Thomas Voit, London (GB)

(73) Assignees: ASSOCIATION INSTITUT DE MYOLOGIE, Paris (FR); INSTITUT NATIONAL DE LA SANTE ET DE LA RECHERCHE MEDICALE, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 0 days.

(21) Appl. No.: 15/327,011

(22) PCT Filed: Jul. 31, 2015

(86) PCT No.: PCT/EP2015/067722
§ 371 (c)(1),
(2) Date: Jan. 17, 2017

(87) PCT Pub. No.: WO2016/016449
PCT Pub. Date: Feb. 4, 2016

(65) Prior Publication Data
US 2017/0152517 A1    Jun. 1, 2017

(30) Foreign Application Priority Data
Jul. 31, 2014  (EP) .................................... 14306228

(51) Int. Cl.
*C07H 21/04*       (2006.01)
*C07H 21/02*       (2006.01)
(Continued)

(52) U.S. Cl.
CPC ........ *C12N 15/1137* (2013.01); *A61K 31/713* (2013.01); *C12N 7/00* (2013.01);
(Continued)

(58) Field of Classification Search
CPC .... C12N 15/111; C12N 15/113; A61K 31/713
See application file for complete search history.

(56) References Cited

U.S. PATENT DOCUMENTS

2016/0076027 A1 * 3/2016 Ward et al. .......... C12N 15/113

FOREIGN PATENT DOCUMENTS

WO          2003/000707 A2     1/2003
WO      WO 03/000707 A2 *     1/2003    .......... C12N 15/111
(Continued)

OTHER PUBLICATIONS

Goyenvalle et al. (Molecular Therapy, vol. 20, No. 6, 2012, pp. 1212-1221).*
(Continued)

*Primary Examiner* — Amy H Bowman
(74) *Attorney, Agent, or Firm* — Arrigo, Lee, Guttman & Mouta-Bellum LLP

(57) ABSTRACT

The invention relates to a method for the treatment of amyotrophic lateral sclerosis (ALS). Specifically, the invention implements the use of an antisense sequence adapted to affect alternative splicing in a human SOD1 pre-mRNA, thereby leading to the destruction of the skipped m RNA by the cell machinery.

34 Claims, 9 Drawing Sheets

Figure 1:
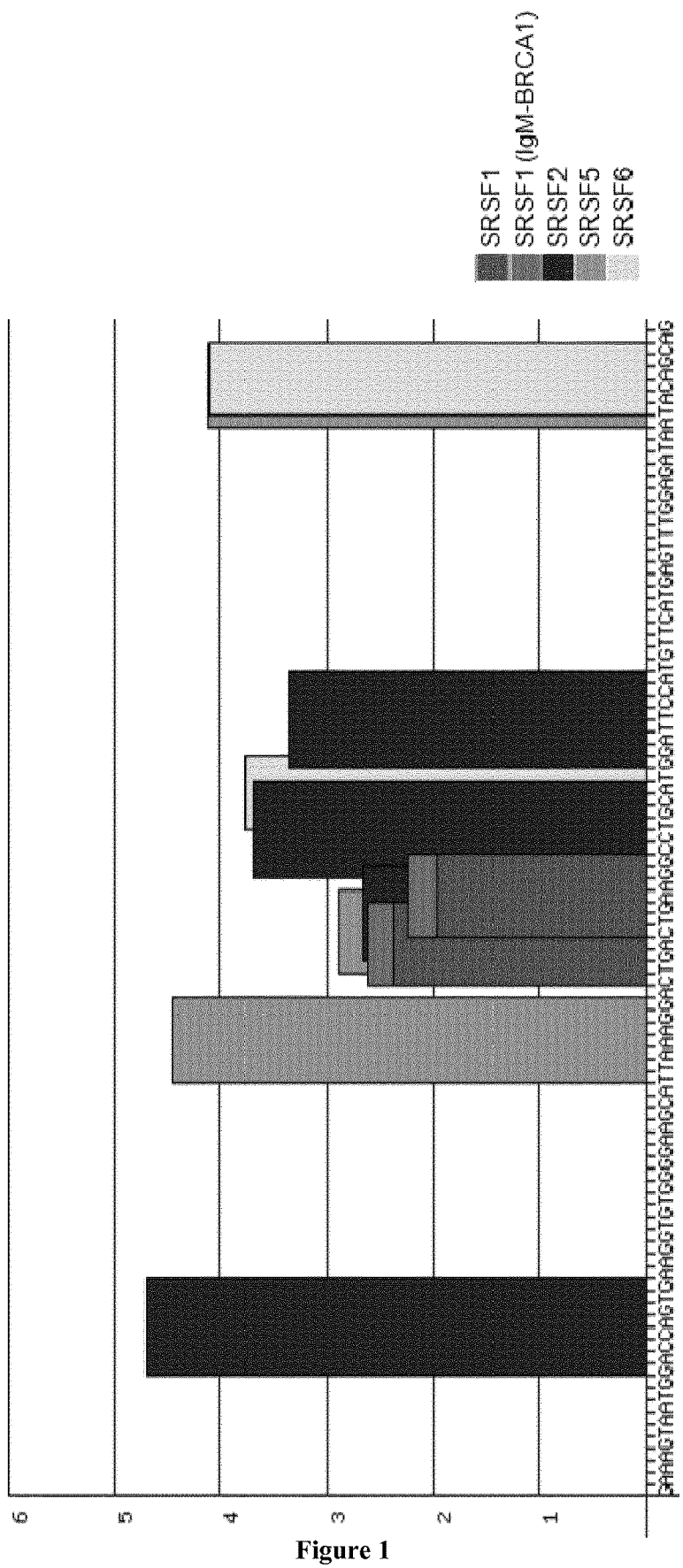

Specification includes a Sequence Listing.

(51) Int. Cl.
*A61K 48/00* (2006.01)
*C12N 15/113* (2010.01)
*A61K 31/713* (2006.01)
*C12N 7/00* (2006.01)
*C12N 15/86* (2006.01)

(52) U.S. Cl.
CPC ...... *C12N 15/86* (2013.01); *C12Y 115/01001* (2013.01); *C12N 2310/11* (2013.01); *C12N 2320/32* (2013.01); *C12N 2320/33* (2013.01); *C12N 2330/51* (2013.01); *C12N 2750/14143* (2013.01); *C12N 2750/14343* (2013.01); *C12N 2799/025* (2013.01)

(56) References Cited

FOREIGN PATENT DOCUMENTS

| WO | 2010/029303 A1 | 3/2010 | | |
|---|---|---|---|---|
| WO | 2013/190059 A1 | 12/2013 | | |
| WO | WO 2015/153800 A2 * | 12/2013 | ........... | C12N 15/115 |
| WO | 2014/172698 A1 | 10/2014 | | |
| WO | 2015/153800 A2 | 10/2015 | | |
| WO | WO 2013/184209 A1 * | 3/2016 | ........... | C12N 15/111 |

OTHER PUBLICATIONS

Ward et al, Nonsense-mediated decay as a terminating mechanism for antisense oligonucleotides, Nucleic Acids Research, vol. 42, No. 9, May 14, 2014 (May 14, 2014), pp. 5871-5879.

Smith et al., Antisense oligonucleotide therapy for neurodegenerative disease, Journal of Clinical Investigation, vol. 116, No. 8, Aug. 1, 2006, pp. 2290-2296.

Morcos, Gene Switching: Analyzing a Broad Range of Mutations Using Steric Block Antisense Oligonucleotides, Methods in Enzymology, Academic Press, US, vol. 313, Jan. 1, 2000, pp. 174-189.

Aartsma-Rus et al, Guidelines for antisense oligonucleotide design and insight into splice-modulating mechanisms, Molecular Therapy, Nature Publishing Group, GB, vol. 17, No. 3, Mar. 1, 2009, pp. 548-553.

European Patent Office, International Search Report for PCT/EP2015/067722, dated Oct. 2, 2015.

* cited by examiner a)

b)

SEQUENCE LISTING

<160> NUMBER OF SEQ ID NOS: 14

<210> SEQ ID NO 1
<211> LENGTH: 20
<212> TYPE: RNA
<213> ORGANISM: artificial
<220> FEATURE:
<223> OTHER INFORMATION: AON1

<400> SEQUENCE: 1
cccacaccuu cacuggucca                                                    20

<210> SEQ ID NO 2
<211> LENGTH: 20
<212> TYPE: RNA
<213> ORGANISM: artificial
<220> FEATURE:
<223> OTHER INFORMATION: AON2

<400> SEQUENCE: 2
ggccuucagu caguccuuua                                                    20

<210> SEQ ID NO 3
<211> LENGTH: 20
<212> TYPE: RNA
<213> ORGANISM: artificial
<220> FEATURE:
<223> OTHER INFORMATION: AON3

<400> SEQUENCE: 3
cugguccauu acuuuccuuu                                                    20

<210> SEQ ID NO 4
<211> LENGTH: 20
<212> TYPE: RNA
<213> ORGANISM: artificial
<220> FEATURE:
<223> OTHER INFORMATION: AON4

<400> SEQUENCE: 4
ccaugcaggc cuucagucag                                                    20

<210> SEQ ID NO 5
<211> LENGTH: 18
<212> TYPE: DNA
<213> ORGANISM: artificial
<220> FEATURE:
<223> OTHER INFORMATION: primer

<400> SEQUENCE: 5
ctagcgagtt atggcgac                                                      18

<210> SEQ ID NO 6
<211> LENGTH: 20
<212> TYPE: DNA
<213> ORGANISM: artificial
<220> FEATURE:
<223> OTHER INFORMATION: primer

<400> SEQUENCE: 6
gccaatgatg caatggtctc                                                    20

<210> SEQ ID NO 7
<211> LENGTH: 20
<212> TYPE: RNA
<213> ORGANISM: artificial

```
<220> FEATURE:
<223> OTHER INFORMATION: control AON

<400> SEQUENCE: 7
gcucauucgc uuucauucuu                                              20

<210> SEQ ID NO 8
<211> LENGTH: 40
<212> TYPE: DNA
<213> ORGANISM: artificial
<220> FEATURE:
<223> OTHER INFORMATION: AON fusion

<400> SEQUENCE: 8
cccacacctt cactggtcca ccatgcaggc cttcagtcag                         40

<210> SEQ ID NO 9
<211> LENGTH: 448
<212> TYPE: DNA
<213> ORGANISM: artificial
<220> FEATURE:
<223> OTHER INFORMATION: U7 + AON

<400> SEQUENCE: 9
taacaacata ggagctgtga ttggctgttt tcagccaatc agcactgact catttgcata    60
gcctttacaa gcggtcacaa actcaagaaa cgagcggttt taatagtctt ttagaatatt   120
gtttatcgaa ccgaataagg aactgtgctt tgtgattcac atatcagtgg aggggtgtgg   180
aaatggcacc ttgatctcac cctcatcgaa agtggagttg atgtccttcc ctggctcgct   240
acagacgcac ttccgcaagc ccacaccttc actggtccac catgcaggcc ttcagtcaga   300 attttttggag caggttttct gacttcggtc ggaaaacccc tcccaatttc actggtctac   360
aatgaaagca aaacagttct cttccccgct ccccggtgtg tgagaggggc tttgatcctt   420
ctctggtttc ctaggaaacg cgtatgtg                                      448

<210> SEQ ID NO 10
<211> LENGTH: 465
<212> TYPE: DNA
<213> ORGANISM: homo sapiens

<400> SEQUENCE: 10
atggcgacga aggccgtgtg cgtgctgaag ggcgacggcc cagtgcaggg catcatcaat    60
ttcgagcaga aggaaagtaa tggaccagtg aaggtgtggg gaagcattaa aggactgact   120
gaaggcctgc atggattcca tgttcatgag tttggagata atacagcagg ctgtaccagt   180
gcaggtcctc actttaatcc tctatccaga aaacacggtg gccaaaagga tgaagagagg   240
catgttggag acttgggcaa tgtgactgct gacaaagatg gtgtggccga tgtgtctatt   300
gaagattctg tgatctcact ctcaggagac cattgcatca ttggccgcac actggtggtc   360
catgaaaaag cagatgactt gggcaaaggt ggaaatgaag aaagtacaaa gacaggaaac   420
gctggaagtc gtttggcttg tggtgtaatt gggatcgccc aataa                   465

<210> SEQ ID NO 11
<211> LENGTH: 459
<212> TYPE: DNA
<213> ORGANISM: artificial
<220> FEATURE:
<223> OTHER INFORMATION: hSOD1 coding gene with silent mutations

<400> SEQUENCE: 11
```

| | |
|---|---|
| gccaccaagg ccgtgtgcgt gctgaagggg gatggacctg tgcagggcat catcaacttc | 60 |
| gagcagaaag aaagcaacgg ccctgtcaaa gtctggggca gcatcaaggg cctcacagag | 120 |
| ggactccacg gcttccacgt gcacgagttc ggcgataata ccgccggctg tacctctgcc | 180 |
| ggccctcact caaccccct gtccagaaaa cacggcggac ccaaggacga ggaacggcac | 240 |
| gtgggcgatc tgggcaatgt gaccgccgac aaagatggcg tggccgacgt gtccatcgag | 300 |
| gacagcgtga tcagcctgag cggcgaccac tgcatcatcg gcagaaccct ggtggtgcac | 360 |
| gagaaggccg atgacctggg caagggcggc aacgaggaaa gcaccaagac aggcaacgcc | 420 |
| ggcagcagac tggcctgtgg cgtgatcgga atcgctcaa | 459 |

```
<210> SEQ ID NO 12
<211> LENGTH: 468
<212> TYPE: DNA
<213> ORGANISM: artificial
<220> FEATURE:
<223> OTHER INFORMATION: hSOD1 coding sequence with silent mutations +
      start and stop codons

<400> SEQUENCE: 12
```

| | |
|---|---|
| atggccacca aggccgtgtg cgtgctgaag ggggatggac ctgtgcaggg catcatcaac | 60 |
| ttcgagcaga agaaaagcaa cggccctgtc aaagtctggg gcagcatcaa gggcctcaca | 120 |
| gagggactcc acggcttcca cgtgcacgag ttcggcgata taccgccgg ctgtacctct | 180 |
| gccggccctc acttcaaccc cctgtccaga aaacacggcg gacccaagga cgaggaacgg | 240 |
| cacgtgggcg atctgggcaa tgtgaccgcc gacaaagatg gcgtggccga cgtgtccatc | 300 |
| gaggacagcg tgatcagcct gagcggcgac cactgcatca tcggcagaac cctggtggtg | 360 |
| cacgagaagg ccgatgacct gggcaagggc ggcaacgagg aaagcaccaa gacaggcaac | 420 |
| gccggcagca gactggcctg tggcgtgatc ggaatcgctc aatgatga | 468 |

```
<210> SEQ ID NO 13
<211> LENGTH: 489
<212> TYPE: DNA
<213> ORGANISM: artificial
<220> FEATURE:
<223> OTHER INFORMATION: Flag-hSOD1opt

<400> SEQUENCE: 13
```

| | |
|---|---|
| atggactaca aagacgatga cgacaaggcc accaaggccg tgtgcgtgct gaaggggggat | 60 |
| ggacctgtgc agggcatcat caacttcgag cagaaagaaa gcaacggccc tgtcaaagtc | 120 |
| tggggcagca tcaagggcct cacagaggga ctccacggct tccacgtgca cgagttcggc | 180 |
| gataataccg ccggctgtac ctctgccggc cctcacttca ccccctgtc agaaaacac | 240 |
| ggcggaccca aggacgagga acggcacgtg ggcgatctgg gcaatgtgac cgccgacaaa | 300 |
| gatggcgtgg ccgacgtgtc catcgaggac agcgtgatca gcctgagcgg cgaccactgc | 360 |
| atcatcggca gaaccctggt ggtgcacgag aaggccgatg acctgggcaa gggcggcaac | 420 |
| gaggaaagca ccaagacagg caacgccggc agcagactgg cctgtggcgt gatcggaatc | 480 |
| gctcaatga | 489 |

```
<210> SEQ ID NO 14
<211> LENGTH: 489
<212> TYPE: DNA
<213> ORGANISM: artificial
<220> FEATURE:
<223> OTHER INFORMATION: hSOD1opt-Flag
```

<400> SEQUENCE: 14

```
atggccacca aggccgtgtg cgtgctgaag ggggatggac ctgtgcaggg catcatcaac        60
ttcgagcaga aagaaagcaa cggccctgtc aaagtctggg gcagcatcaa gggcctcaca       120
gagggactcc acggcttcca cgtgcacgag ttcggcgata ataccgccgg ctgtacctct       180
gccggccctc acttcaaccc cctgtccaga aaacacggcg gacccaagga cgaggaacgg       240
cacgtgggcg atctgggcaa tgtgaccgcc gacaaagatg gcgtggccga cgtgtccatc       300
gaggacagcg tgatcagcct gagcggcgac cactgcatca tcggcagaac cctggtggtg       360
cacgagaagg ccgatgacct gggcaagggc ggcaacgagg aaagcaccaa gacaggcaac       420
gccggcagca gactggcctg tggcgtgatc ggaatcgctc aagactacaa agacgatgac       480
gacaagtga                                                               489
```

TREATMENT OF AMYOTROPHIC LATERAL SCLEROSIS

FIELD OF THE INVENTION

The invention relates to a method for the treatment of amyotrophic lateral sclerosis (ALS). Specifically, the invention implements the use of an antisense sequence adapted to affect alternative splicing in a human SOD1 pre-mRNA, thereby leading to the destruction of the skipped mRNA by the cell machinery.

BACKGROUND OF THE INVENTION

Amyotrophic Lateral Sclerosis (ALS) is epidemiologically classified into sporadic (90%-95%) and familial (5%-10%) forms (Rosen et al., 1993). Twenty percent of the familial forms (fALS) are caused by mutations in the Superoxide Dismutase 1 (SOD1) gene. The function of the SOD1 metalloenzyme is to convert superoxide, a toxic by-product of mitochondrial oxidative phosphorylation, to molecular oxygen or hydrogen peroxide. Mutant SOD1 possesses a neurotoxic property (toxic gain of function) that is responsible for the pathogenic mechanism of the disease. Indeed, transgenic mice overexpressing mutant forms of the human SOD1 gene (for example SOD1$^{G93A}$ mice) recapitulate most pathological features of ALS and are widely used in ALS preclinical studies (Gurney et al., 1994). Decreasing the accumulation of SOD1 has thus arisen as a logical strategy to treat SOD1-linked forms of fALS. Attractive molecular approaches have been developed to downregulate almost any gene in the central nervous system (CNS), mainly based on the use of antisense oligonucleotides (AONs) (Crooke, 2004) or RNA interference with either siRNA (Dorn et al., 2004) or synthetic microRNA (Boudreau et al., 2011).

Suppression of mutant SOD1 expression using siRNA has first proved significant therapeutic efficiency in SOD1-linked ALS mice. Raoul et al. showed that intraspinal injection of lentiviral vectors encoding short hairpin RNAs (shRNAs) to human SOD1 delayed disease onset and progression in SOD1$^{G93A}$ mice (Raoul et al., 2005). Independently, Ralph et al., demonstrated that intramuscular injections of lentivirus mediating the expression of RNAi to the human SOD1, prevented neurodegeneration and extended survival in the same ALS mouse model, leading to a maximal 77% lifespan increase (Ralph et al., 2005).

Continuous infusion of an AON inducing enzyme-mediated decay into the brain ventricles has also been reported to allow efficient and widespread reduction of both SOD1 mRNA and protein levels throughout the brain and the spinal cord, significantly slowing disease progression in a rat model of ALS caused by the SOD1$^{G93A}$ mutation (Smith et al., 2006).

However, this method necessitated surgically implantation of a catheter through the skull, connected to an osmotic pump and its therapeutic efficacy was limited (9.1% extension survival with a treatment beginning at 65 days of age) (Smith et al., 2006). Based on this discovery, a multicenter clinical trial of AONs infusion into ALS patient's cerebrospinal fluid (CSF) was initiated by Isis Pharmaceuticals, showing the feasibility and the lack of adverse effects of the treatment (Miller et al., 2013). More recently, steric blocking AONs were also used to promote aberrant exon-skipping (and generation of premature stop codon containing mRNAs), as an alternative method to decrease mouse Sod1 levels in the CNS of wild type mice (Ward et al., 2014).

However, the intracerebroventricular (ICV) injection of 2'-MOE AONs targeting mouse Sod1 pre-mRNA caused only a weak skipping of Sod1 exon 2 and exon 3 in the brain and spinal cord, leading to 25-50% reduction of Sod1 levels, similarly to the level achieved with the same dose of the previously used RNase H-dependent 2'-MOE gapmer AONs in SOD1$^{G93A}$ rats (Smith et al., 2006). From these results, lifespan improvement would have been expected to be, at most, equivalent to that obtained with enzyme-mediated strategies such as RNAi or gapmer strategies.

In addition, the immediate challenge facing fALS therapies based on SOD1 suppression is the widespread delivery of the silencing instructions to all affected cells. In 2007, we discovered that, despite the blood-brain-barrier, systemic delivery of self-complementary adeno-associated virus vectors of serotype 9 (scAAV9) allowed transduction of both CNS and peripheral cells in mice and cats, including in the cell types suspected to be involved in ALS (neurons, astrocytes, and muscle cells) (Duque et al., 2009) (EP2212424). More recently, the rh10 serotype (AAV10) was also found efficient for systemic transduction of CNS and peripheral tissues after IV injection in mice and marmosets (Hu et al., 2010; Yang et al., 2014; Zhang et al., 2011).

Recently, the efficiency of AAV-based gene therapy strategies for ALS has been demonstrated in two studies using RNA interference to reduce SOD1 levels. Foust et al. first obtained a 38% of survival extent in ALS mice following intravenous (IV) injection of neonates with an AAV9-shRNA targeting SOD1 (Foust et al., 2013). Furthermore, intrathecal (IT) injection of an AAV10-shRNA-SOD1 in post-symptomatic 55-days old SOD1 mice resulted in 22% of increased survival in ALS mice (Wang et al., 2013).

In view of the limited therapeutic achievements reported in these previous studies, technology improvements for ALS biotherapy are still needed.

SUMMARY OF THE INVENTION

The present invention stems from the unexpected finding that the survival of a mouse model of ALS can be greatly improved, in comparison to the ALS therapeutic strategies of the prior art, when mice are administered with an antisense oligonucleotide that is adapted to induce exon skipping in the human SOD1 pre-mRNA.

Ward et al. (cited above) reported that decrease in the expression of SOD1 using an exon-skipping strategy would at most be equivalent to the decrease obtained with a gapmer, i.e. with an antisens oligonucleotide that decreases the level of SOD1 not by nonsense-mediated mRNA decay but through an RNase H mechanism. The decrease in SOD1 mRNA and protein levels reported in Ward et al. was also equivalent to that obtained with strategies involving the RISC mechanism (such as strategies using RNAi and shRNAs). Thus, one skilled in the art would have expected that lifespan improvement resulting from using a SOD1 exon-skipping strategy would be equivalent to that reported in previous studies. The present inventors have unexpectedly shown that a survival extent of up to 134%, and even more, may result from the administration of an antisense oligonucleotide that is adapted to induce exon skipping in the human SOD1 pre-mRNA. This survival extent is the highest reported to date in SOD1-linked ALS mice and is far more efficient than previous SOD1-silencing strategies (reporting a maximum of 38% of survival extent), showing the originality and superiority of this molecular approach, which was not expected from the previously reported studies.

Accordingly, disclosed herein is a method for the treatment of ALS, comprising administering to a subject in need thereof an antisense oligonucleotide adapted to induce exon-skipping in a human SOD1 pre-mRNA, thereby inducing degradation of the resulting skipped human SOD1-coding mRNA.

Another object disclosed herein is an antisense oligonucleotide specific of a human SOD1 pre-mRNA sequence, said antisense oligonucleotide being adapted to induce skipping of an exon in said pre-mRNA.

Another object disclosed herein is an antisense oligonucleotide specific of a human SOD1 pre-mRNA, for use in a method for the treatment of ALS, wherein said antisense oligonucleotide is adapted to induce skipping of an exon in said pre-mRNA.

DETAILED DESCRIPTION OF THE INVENTION

The present invention relates to antisense oligonucleotides (AONs) useful for treating human subjects suffering from ALS. The subject suffers from sporadic or familial forms of ALS caused by mutations in the SOD1 gene or in other ALS-linked genes, for example in ALS-linked genes that result in an increase of SOD1 mRNA levels (ALS online database ALSoD, http://alsod.iop.kcl.ac.uk, April 2014). The subject may be at the pre-symptomatic or symptomatic stage of the disease.

In the present application, "antisense oligonucleotide", or "AON" denotes a single stranded nucleic acid sequence, either DNA or RNA (Chan et al., 2006), which is complementary to a part of a pre-mRNA coding the SOD1 protein. In particular, the AON of the present invention is designed to block a splice acceptor (SA) site and/or an exon splicing enhancer (ESE) and/or a branch point in the SOD1 pre-mRNA and/or any sequence which could modulate pre-mRNA splicing, i.e. it is designed to be complementary to a part of the SOD1 pre-mRNA comprising an SA, an ESE, a branch point sequence or any sequence which could modulate pre-mRNA splicing (Cartegni et al., 2002; Reed and Maniatis, 1988).

The AON is used for inducing exon-skipping within a SOD1 pre-mRNA, thereby leading to a frameshift which produces a truncated cDNA containing a premature stop codon in the resulting mRNA. This strategy thus allows the reduction of the level of an otherwise neurotoxic protein that is responsible for the pathogenic mechanism of ALS.

The human SOD1 gene (hSOD1) is well characterized. Its sequence is reported in (Gene ID: 6647; NCBI reference sequence, accession number NM 000454.4; SEQ ID NO:10).

An AON according to the invention is of the type that induces exon-skipping in the human SOD1 pre-mRNA. For example, the implemented AON may be designed to specifically induce exon 2, exon 3 or exon 4 skipping. In a particular embodiment, the AON of the present invention is able to induce the inclusion of a premature stop codon in the human SOD1 mRNA. Preferably, the AON is adapted to induce exon 2 skipping. As provided in the examples, exon 2 skipping induces a frameshift which leads to a premature stop codon in exon 4.

Tools are available for identifying SA, ESE and branch point sequences in a pre-mRNA of interest. As is well known by those skilled in the art, SA are conserved sequences, they are at the 3' end of the intron and terminates the intron with an almost invariant AG sequence. In addition, ESE motifs may be predicted on the exon sequence intended to be skipped using the ESEfinder software tool (http://rulai.cshl.edu/cgi-bin/tools/ESE3/esefinder.cgi?process=home).

Design of the AON can then be carried out following the rules published in Aartsma-Rus et al. (Aartsma-Rus et al., 2009).

The AON of the invention is designed to complement suitable sequences within the human SOD1 (hSOD1) pre-mRNA which are required for correct splicing of the targeted exon, thereby blocking splicing reactions that would incorporate the targeted exon into mature mRNA.

The AON of the invention may be of any suitable type. Representative AON types include oligodeoxyribonucleotides, oligoribonucleotides, morpholinos, tricyclo-DNA-antisense oligonucleotides, tricyclo-phosphorothioate DNA oligonucleotides, LNA, small nuclear RNA-modified such as U7-, U1- or U6-modified AONs (or other UsnRNPs), or conjugate products thereof such as peptide-conjugated or nanoparticle-complexed AONs.

AONs employed in the practice of the invention are generally from about 10 to about 30 nucleotides in length, and may be for example, about 10, or about 15, or about 20 or about 30 or about 40 nucleotides or more in length depending on the targeted sequences within the human SOD1 pre-mRNA and the AON chemistry.

Representative AONs for practice of the present invention are listed in table 1:

| AON1 | 5' CCCACACCUUCACUGGUCCA 3' | SEQ ID NO: 1 |
|---|---|---|
| AON2 | 5' GGCCUUCAGUCAGUCCUUUA 3' | SEQ ID NO: 2 |
| AON3 | 5' CUGGUCCAUUACUUUCCUUU 3' | SEQ ID NO: 3 |
| AON4 | 5' CCAUGCAGGCCUUCAGUCAG 3' | SEQ ID NO: 4 |

In a particular embodiment, the AON for practice of the invention is selected from SEQ ID NO:1 and 4. In a further embodiment, both sequences shown in SEQ ID NO:1 and 4 are included in the AON of the invention.

For use in vivo, the AONs may be stabilized, for example via phosphate backbone modifications. For example, stabilized AONs of the instant invention may have a modified backbone, e.g. have phosphorothioate linkages. Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the AONs also include "Morpholinos" (phosphorodiamidate morpholino oligomers, PMOs), 2'-O-Methyl oligomers, tricyclo-DNAs, tricyclo-DNA-phosphorothioate AON molecules (WO2013/053928) or U small nuclear (sn) RNAs. The latter forms of AONs that may be used to this effect can be coupled to small nuclear RNA molecules such as U1, U6 or U7 (or other UsnRNPs), in particular in combination with a viral transfer method based on, but not limited to, lentivirus, retrovirus or adeno-associated virus. In a particular embodiment, the AON used in the present invention comprises both the sequence of SEQ ID NO:1 and SEQ ID NO:4. In addition, in a further particular embodiment, the AON comprises a small nuclear molecule such as U1, U6 or U7 (or other UsnRNPs), in particular U7, and includes the sequence shown in SEQ ID NO:1 and SEQ ID NO:4. Such AON is represented in SEQ ID NO:9.

For stable and efficient in vivo delivery, through the blood-brain-barrier in particular, the AONs may also be fused to or co-administered with any cell-penetrating peptide and to signal peptides mediating protein secretion. Cell-penetrating peptides can be RVG peptides (Kumar et al., 2007), PiP (Betts et al., 2012), P28 (Yamada et al., 2013), or protein transduction domains like TAT (Malhotra et al., 2013) or VP22 (Lundberg et al., 2003) Antisense sequences of the invention may be delivered in vivo alone or in association with a vector. In its broadest sense, a "vector" is any vehicle capable of facilitating the transfer of the antisense sequence to the cells and preferably cells expressing SOD1. Preferably, the vector transports the antisense sequence to cells with reduced degradation relative to the extent of degradation that would result in the absence of the vector. In general, the vectors useful in the invention include, but are not limited to, plasmids, phagemids, viruses, and other vehicles derived from viral or bacterial sources that have been manipulated by the insertion or incorporation of the AON sequences. Viral vectors are a preferred type of vector and include, but are not limited to, nucleic acid sequences from the following viruses: lentivirus such as HIV-1, retrovirus, such as moloney murine leukemia virus, adenovirus, adeno-associated virus (AAV); SV40-type viruses; Herpes viruses such as HSV-1 and vaccinia virus. One can readily employ other vectors not named but known in the art. Among the vectors that have been validated for clinical applications and that can be used to deliver the antisense sequences, lentivirus, retrovirus and AAV show a greater potential for exon skipping strategy.

Retrovirus-based and lentivirus-based vectors that are replication-deficient (i.e., capable of directing synthesis of the desired AON, but incapable of producing an infectious particle) have been approved for human gene therapy trials. They have the property to integrate into the target cell genome, thus allowing for a persistent transgene expression in the target cells and their progeny.

In a preferred embodiment, the AON is delivered using an AAV vector. The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter). AAV-based recombinant vectors lack the Rep protein and integrate with low efficacy and are mainly present as stable circular episomes that can persist for months and maybe years in the target cells. Therefore AAV has aroused considerable interest as a potential vector for human gene therapy. Among the favorable properties of the virus are its lack of association with any human disease and the wide range of cell lines derived from different tissues that can be infected. Actually 12 AAV serotypes (AAV1 to 12) and up to 120 variants are known (Gao et al., 2004; Gao et al., 2002), each with different tissue tropisms. Accordingly, the present invention relates to an AAV vector comprising the AON described above, targeting a human SOD1 pre-mRNA and adapted to induce exon-skipping in said human SOD1 pre-mRNA. According to a particular embodiment, the AAV genome is derived from an AAV1, 2, 3, 4, 5, 6, 7, 8, 9, 10 (e.g. cynomolgus AAV10 or rhesus monkey AAVrh10), 11 or 12 serotype. In a preferred embodiment, the AAV capsid is derived from an AAV1, 2, 3, 4, 5, 6, 7, 8, 9, 10 (e.g. cynomolgus AAV10 or AAVrh10), 11, 12, serotype or AAV variants. In a further particular embodiment, the AAV vector is a pseudotyped vector, i.e. its genome and capsid are derived from AAVs of different serotypes. For example, the pseudotyped AAV vector may be a vector whose genome is derived from the AAV2 serotype, and whose capsid is derived from the AAV1, 3, 4, 5, 6, 7, 8, 9, 10 (e.g. cynomolgus AAV10 or AAVrh10), 11, 12 serotype or from AAV variants. In addition, the genome of the AAV vector may either be a single stranded or self-complementary double-stranded genome (McCarty et al., 2001). Self-complementary double-stranded AAV vectors are generated by deleting the terminal resolution site (trs) from one of the AAV terminal repeats. These modified vectors, whose replicating genome is half the length of the wild type AAV genome have the tendency to package DNA dimers.

Preferably, the AAV vector implemented in the practice of the present invention is a vector targeting CNS neurons (including motor neurons and glial cells in the brain, brainstem and spinal cord) and muscle cells (Ilieva et al., 2009). In a preferred embodiment, the AAV vector has an AAV1, AAV6, AAV6.2, AAV7, AAVrh39, AAVrh43, AAV2, AAV5, AAV8, AAV9 or AAV10 capsid, this vector being optionally pseudotyped. In a particular embodiment, the AAV vector has an AAV9 or AAV10 (e.g. cynomolgus AAV10 or AAVrh10) capsid and is optionally pseudotyped.

In a particular embodiment, the AON as described above is linked to a small nuclear RNA molecule such as a U1, U2, U6, U7 or any other small nuclear RNA, or chimeric small nuclear RNA (Cazzella et al., 2012; De Angelis et al., 2002). Information on U7 modification can in particular be found in Goyenvalle, et al. (Goyenvalle et al., 2004); WO11113889; and WO06021724. In a particular embodiment, the U7 cassette described by D. Schumperli is used (Schumperli and Pillai, 2004). It comprises the natural U7-promoter (position −267 to +1), the U7smOpt snRNA and the downstream sequence down to position 116. The 18 nt natural sequence complementary to histone pre-mRNAs in U7smOpt is replaced by one or two (either the same sequence used twice, or two different sequences) or more repeats of the selected AON sequences using, for example, PCR-mediated mutagenesis, as already described (Goyenvalle et al., 2004).

In a particular embodiment, the small nuclear RNA-modified AONs, in particular the U7-modified AONs, are vectorized in a viral vector, more particularly in an AAV vector.

Typically, the vector may also comprise regulatory sequences allowing expression of the encoded AONs, such as e.g., a promoter, enhancer internal ribosome entry sites (IRES), sequences encoding protein transduction domains (PTD), and the like. In this regard, the vector most preferably comprises a promoter region, operably linked to the coding sequence, to cause or improve expression of the AON. Such a promoter may be ubiquitous, tissue-specific, strong, weak, regulated, chimeric, etc., to allow efficient and suitable production of the AON. The promoter may be a cellular, viral, fungal, plant or synthetic promoter. Most preferred promoters for use in the present invention shall be functional in nervous and muscle cells, more preferably in motor neurons and glial cells. Promoters may be selected from small nuclear RNA promoters such as U1, U2, U6, U7 or other small nuclear RNA promoters, or chimeric small nuclear RNA promoters. Other representative promoters include RNA polymerase III-dependent promoters, such as the H1 promoter, or RNA polymerase II-dependent promoters. Examples of regulated promoters include, without limitation, Tet on/off element-containing promoters, rapamycin-inducible promoters and metallothionein promoters. Examples of promoters specific for the motor neurons include the promoter of the Calcitonin Gene-Related Peptide (CGRP), the Choline Acetyl Transferase (ChAT), or the Homeobox 9 (HB9). Other promoters functional in motor neurons include neuron-specific such as promoters of the Neuron Specific Enolase (NSE), Synapsin, or ubiquitous promoters including Neuron Specific Silencer Elements (NRSE). Promoters specific of glial cells, such as the promoter of the Glial Fibrillary Acidic Protein (GFAP), can also be used. Examples of ubiquitous promoters include viral promoters, particularly the CMV promoter, the RSV promoter, the SV40 promoter, hybrid CBA (Chicken beta actin/CMV) promoter, etc. and cellular promoters such as the PGK (phosphoglycerate kinase) or EF1alpha (Elongation Factor 1alpha) promoters.

In a particular embodiment, the AON used in the present invention is vectorized in a viral vector, in particular an AAV vector, more particularly an AAV9 or AAV10 (such as a cynomolgus AAV10 or AAVrh10) vector, and comprises both the sequence of SEQ ID NO:1 and SEQ ID NO:4. In addition, in a further particular embodiment, the vectorized AON comprises a small nuclear molecule such as U1, U6 or U7 (or other UsnRNPs), in particular U7, and include the sequence shown in SEQ ID NO:1 and SEQ ID NO:4. Such AON is represented in SEQ ID NO:9.

In a particular embodiment of the invention, referred to as "erase-replace" in the experimental section below, the AON as described above is for administration in association with an expression cassette containing a gene coding for a wild-type SOD1 protein, in particular a human SOD1 protein. The exogenous expression of the SOD1 protein may be provided to optionally compensate the lack of endogenous wild-type SOD1 mRNA resulting from the AON delivery, which does not target specifically the mutated form of the human SOD1 mRNA but can also induce silencing of the wild-type protein. In this embodiment, the gene coding for the wild-type SOD1 protein (preferentially the wild-type human protein) is designed to comprise silent mutations (i.e. mutations that do not affect the amino acid primary sequence of the SOD1 protein) which would impair hybridization of the AON to the corresponding mRNA, thereby avoiding exon skipping in said exogenous SOD1 mRNA. Therefore, in one of its aspect, the invention relates to a gene coding for a wild-type SOD1 protein, such as a human wild-type SOD1 protein, which is designed to comprise silent mutations resulting in impairing the hybridization of an AON of the present invention to a mRNA encoded by this gene. In a particular embodiment, the gene coding for the wild-type SOD1 protein comprises the sequence shown in SEQ ID NO:11 which is a human SOD1 sequence modified with silent mutations as provided above (of note, this sequence does not comprise a start and stop codon). The sequence of SEQ ID NO:11 may further comprise a start codon and a stop codon, such as in the sequence shown in SEQ ID NO:12. In addition, the gene may encode a tagged wild-type SOD1 protein, such as a Flag-tagged SOD1 protein the tag being provided either at the N-terminal or C-terminal end of the SOD1 protein. Such genes coding Flag-hSOD1 or hSOD1-Flag are shown in SEQ ID NO:13 and 14. The expression cassette may comprise regulatory sequences allowing expression of the encoded exogenous SOD1 protein, such as e.g., a promoter, enhancer internal ribosome entry sites (IRES), sequences encoding protein transduction domains (PTD), and the like. In this regard, the vector most preferably comprises a promoter region, operably linked to the coding sequence, to cause or improve expression of the protein. Such a promoter may be ubiquitous, tissue-specific, strong, weak, regulated, chimeric, etc., to allow efficient and suitable production of the protein. The promoter may be a cellular, viral, fungal, plant or synthetic promoter. Most preferred promoters for use in the present invention shall be functional in nervous and muscle cells, more preferably in motor neurons and glial cells. Examples of regulated promoters include, without limitation, Tet on/off element-containing promoters, rapamycin-inducible promoters and metallothionein promoters. Examples of promoters specific for the motor neurons include the promoter of the Calcitonin Gene-Related Peptide (CGRP), the Choline Acetyl Transferase (ChAT), or the Homeobox 9 (HB9. Other promoters functional in motor neurons include neuron-specific such as promoters of the Neuron Specific Enolase (NSE), Synapsin, or ubiquitous promoters including Neuron Specific Silencer Elements (NRSE). Promoters specific of glial cells, such as the promoter of the Glial Fibrillary Acidic Protein (GFAP), can also be used. Examples of ubiquitous promoters include viral promoters, particularly the CMV promoter, the RSV promoter, the SV40 promoter, hybrid CBA (Chicken beta actin/CMV) promoter, etc. and cellular promoters such as the PGK (phosphoglycerate kinase) or EF1alpha (Elongation Factor 1alpha) promoters. The expression cassette may be included into an appropriate vector, such as those vectors described above. In a particular embodiment, the vector containing the expression cassette is a viral vector, in particular a viral vector capable of transducing motor neurons and muscle cells, such as those described above, and in particular such as an AAV vector, in particular an AAV vector comprising an AAV9 or AAV10 (e.g. cynomolgus AAV10 or AAVrh10) capsid. In a variant of this embodiment, the cassettes encoding the AON and the exogenous SOD1 gene, in particular the human SOD1, are both contained in the same vector, in particular a viral vector, in particular a viral vector capable of transducing motor neurons and muscle cells, such as those described above, and in particular such as an AAV vector, in particular an AAV vector comprising an AAV9 or AAV10 (e.g. cynomolgus AAV10 or AAVrh10) capsid.

The invention also relates to a composition comprising an AON, or a vector comprising the same, and/or an exogenous SOD1 cDNA, or a vector comprising an expression cassette encoding an exogenous SOD1 protein, as described above, in a pharmaceutically acceptable carrier. In addition to the AON or to the vector, a pharmaceutical composition of the present invention may also include a pharmaceutically or physiologically acceptable carrier such as saline, sodium phosphate, etc. The composition will generally be in the form of a liquid, although this needs not always to be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, mineral oil, etc. The formulation can also include lubricating agents, wetting agents, emulsifying agents, preservatives, buffering agents, etc. In particular, the present invention involves the administration of an AON and is thus somewhat akin to gene therapy. Those of skill in the art will recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

The compositions of the invention are generally administered via enteral or parenteral routes, e.g. intravenously (i.v.), intra-arterially, subcutaneously, intramuscularly (i.m.), intracerebrally, intracerebroventricularly (i.c.v.), intrathecally (i.t.), intraperitoneally (i.p.), although other types of administration are not precluded, e.g. via inhalation, intranasally, topical, per os, rectally, intraosseous, eye drops, ear drops administration, etc.

In a particular embodiment, an AAV vector of the invention is administered by combining an administration in the cerebrospinal fluid (CSF) and in the blood of the patient, as is described in WO2013/190059. In a particular variant of this embodiment, administration of the viral vector into the CSF of the mammal is performed by intracerebroventricular (i.c.v. or ICV) injection, intrathecal (i.t. or IT) injection, or intracisternal injection, and administration into the blood is preferably performed by parenteral delivery, such as i.v. (or IV) injection, i.m. injection, intra-arterial injection, i.p. injection, subcutaneous injection, intradermal injection, nasal delivery, transdermal delivery (patches for examples), or by enteral delivery (oral or rectal). In a particular embodiment, the AAV vector is administered via both the i.c.v. (or i.t.) and i.v. (or i.m.) routes.

Injectable preparations, for example, sterile injectable aqueous or oleaginous suspensions may be formulated according to the known art using suitable dispensing or wetting agents and suspending agents. The sterile injectable preparation can also be a sterile injectable solution or suspension in a nontoxic parenterally acceptable diluent or solvent, for example, as a solution in 1,3-butanediol. While delivery may be either local (i.e. in situ, directly into tissue such as muscle tissue) or systemic, usually delivery will be local to affected muscle tissue, e.g. to skeletal muscle, smooth muscle, heart muscle, etc. Depending on the form of the AONs that are administered and the tissue or cell type that is targeted, techniques such as electroporation, sonoporation, a "gene gun" (delivering nucleic acid-coated gold particles), etc. may be employed.

One skilled in the art will recognize that the amount of an AON or of a vector containing or expressing the AON and/or the exogenous SOD1 protein to be administered will be an amount that is sufficient to induce amelioration of unwanted ALS symptoms. Such an amount may vary inter alia depending on such factors as the gender, age, weight, overall physical condition of the patient, etc. and may be determined on a case by case basis. The amount may also vary according to other components of a treatment protocol (e.g. administration of other medicaments, etc.). Generally, a suitable dose is in the range of from about 1 mg/kg to about 100 mg/kg, and more usually from about 2 mg/kg/day to about 10 mg/kg. If a viral-based delivery of AON is chosen, suitable doses will depend on different factors such as the virus that is employed, the route of delivery (intramuscular, intravenous, intra-arterial or other), but may typically range from 10e9 to 10e15 viral particles/kg. Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient may be a single event (with modified AONs or AAV vectors), or the patient is administered with the AON on multiple occasions, that may be, depending on the results obtained, several days apart, several weeks apart, or several months apart, or even several years apart.

The methods of the present invention can be implemented in any of several different ways. For example, the AONs of the present invention may be administered together with AONs designed to remove other exons, or siRNAs, or miRNAs (e.g. in a single mixture, or in separate mixtures but administered in close temporal proximity, such as one directly after the other-in any order-with only a few minutes or hours between administrations). They may also be administered, as described above, together with a vector encoding an exogenous SOD1 protein, preferentially a human SOD1 protein, whose coding sequence has been designed to make its encoded mRNA resistant to the AON-induced exon-skipping.

In a further aspect, the invention relates to a kit-of-parts, comprising:
  an AON of the present invention, or a vector coding said AON, as described above; and
  a vector coding for a wild-type SOD1 protein (such as a wild-type human SOD1 protein, whose coding sequence is designed to make its encoded mRNA resistant to the AON-induced exon-skipping;
  for their simultaneous, separate or sequential use in cytostatic therapy Further aspects and advantages of the present inventions will be disclosed in the following experimental section, which shall be considered as illustrative only, and not limiting the scope of this application.

LEGEND TO THE FIGURES

FIG. 1: Graphic Representation of potential ESE motif predicted by ESEfinder in exon 2hSOD1. Threshold values are default defined by the software. SRF1 (SF2/ASF): 1.956; SRF1 (IgM-BRCA1): 1.867; SRF2 (SC35): 2.382; SRF5 (SRp40): 2.67; SRF6 (SRp55): 2.676. SEQ ID NO:10, nucleotides 73-169, is shown.

Figure 2:
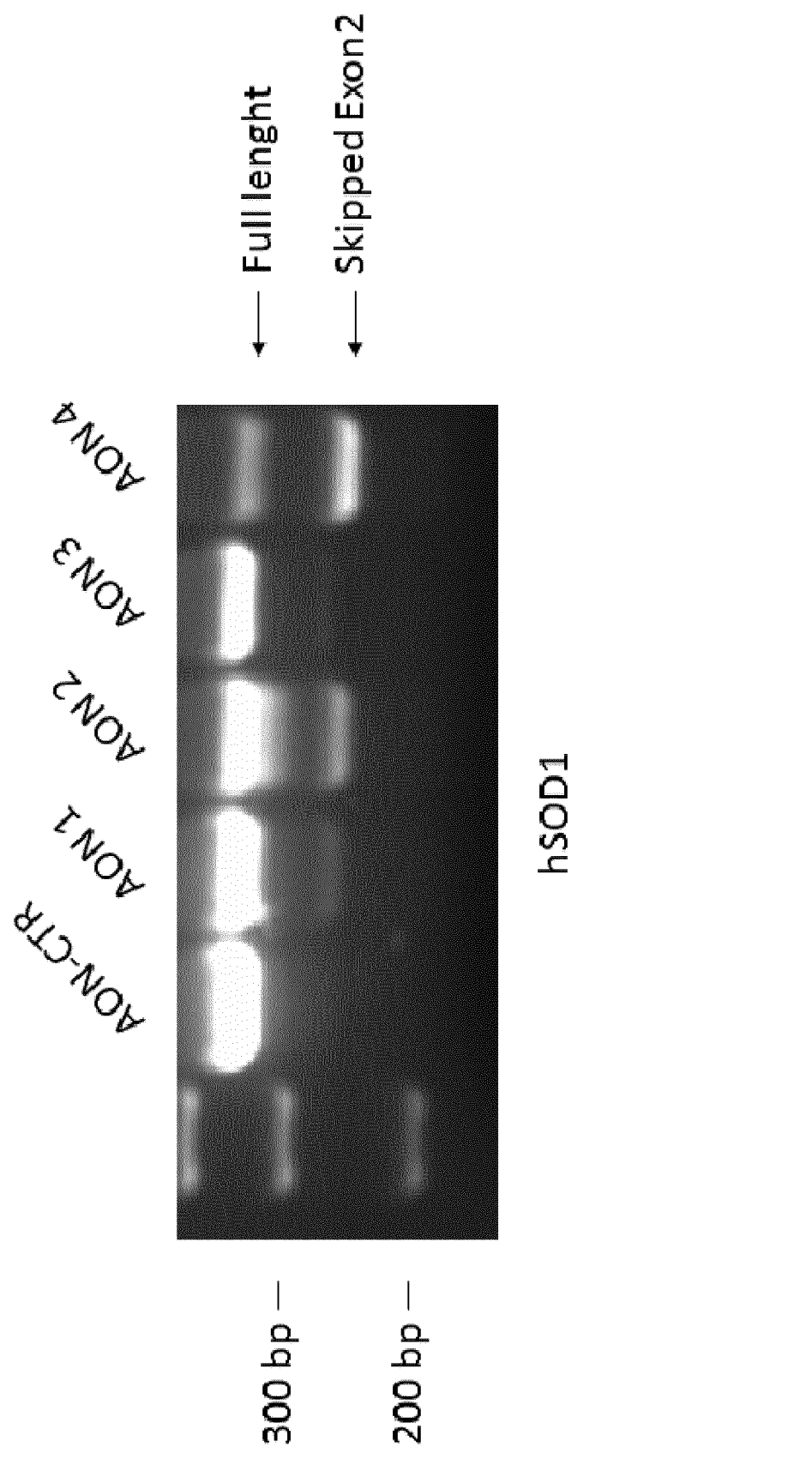

FIG. 2: RT-PCR on AON transfected 293T cells.

Figure 3:
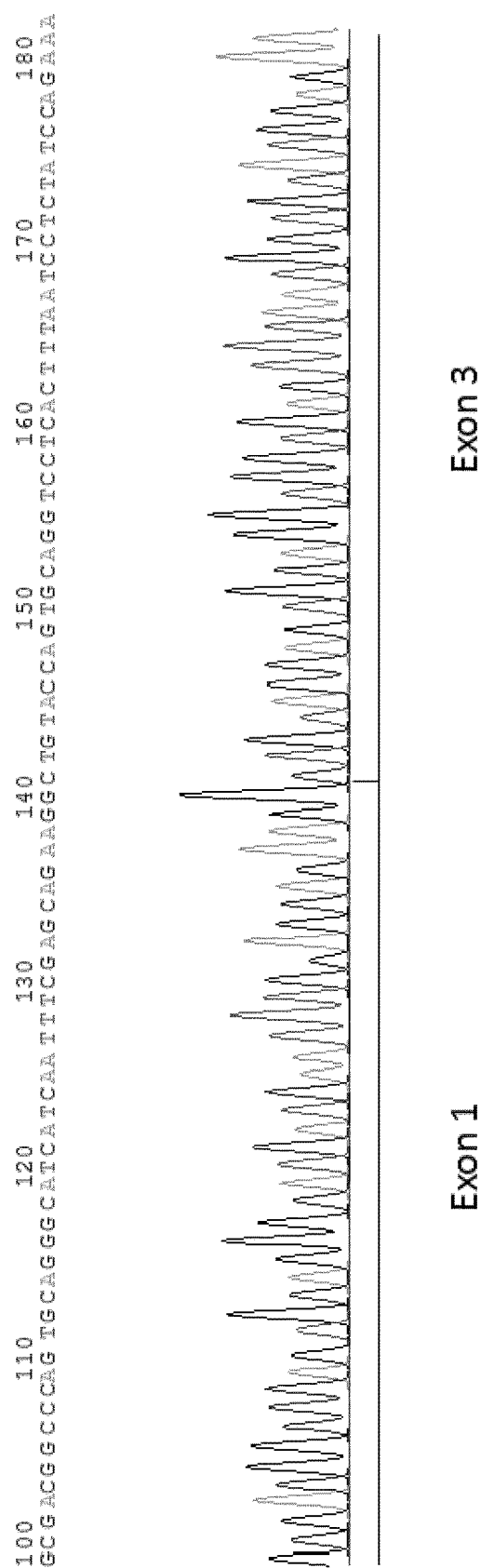

FIG. 3: Sequencing of the skipped form. SEQ ID NO:10, nucleotides 31-73 and 171-212, is shown.

Figure 4:
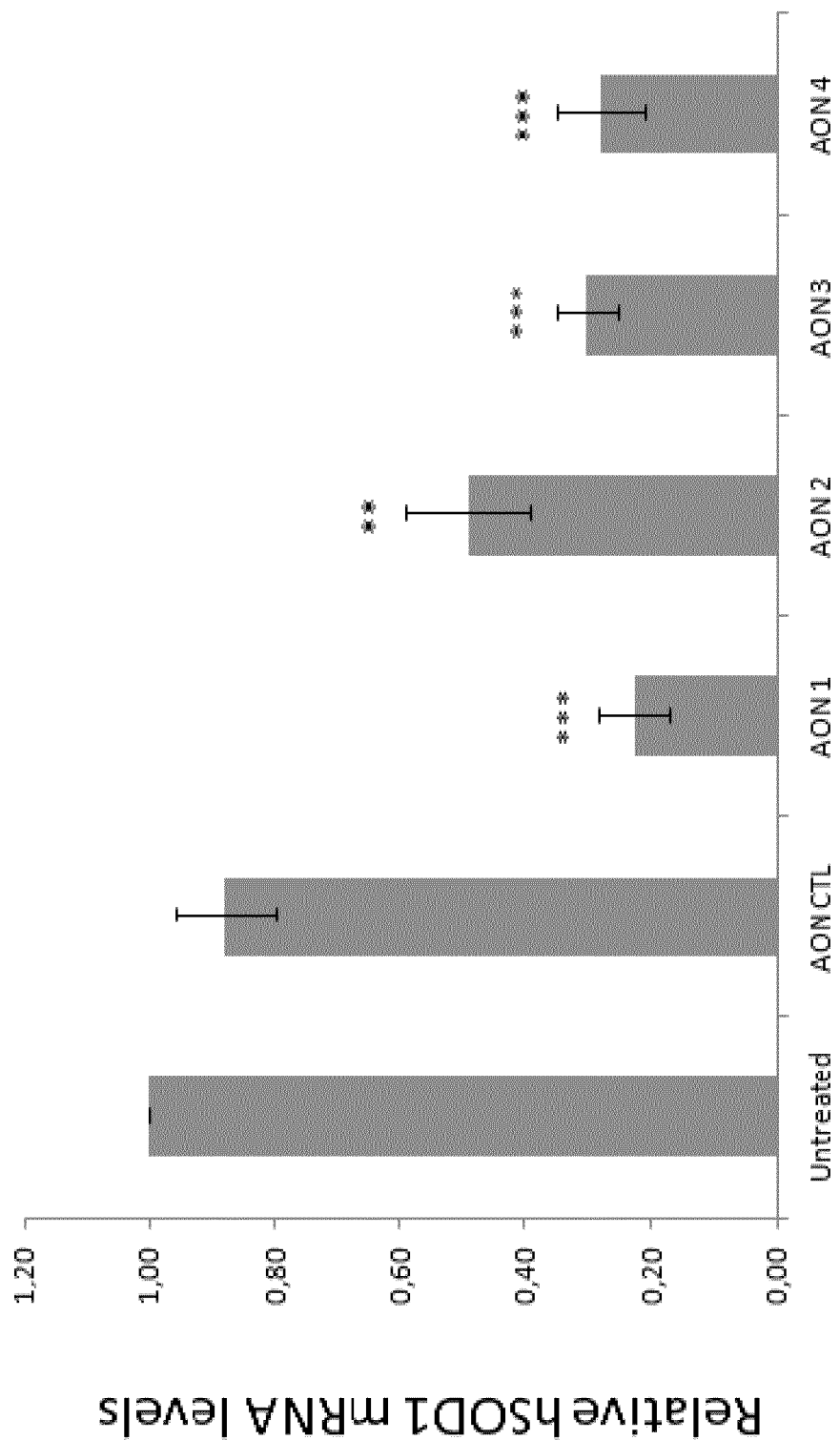

FIG. 4: Full length hSOD1 mRNA expression in transfected cells. Percentage of hSOD1 reduction of each AON, compared to untreated cells: AON1: 85%; AON2: 55%; AON3: 75%; AON4: 81%. Data are means+/−SEM (n=3). P<0.01, *P<0.005, determined by Student's t-test compared to untreated cells.

Figure 5:
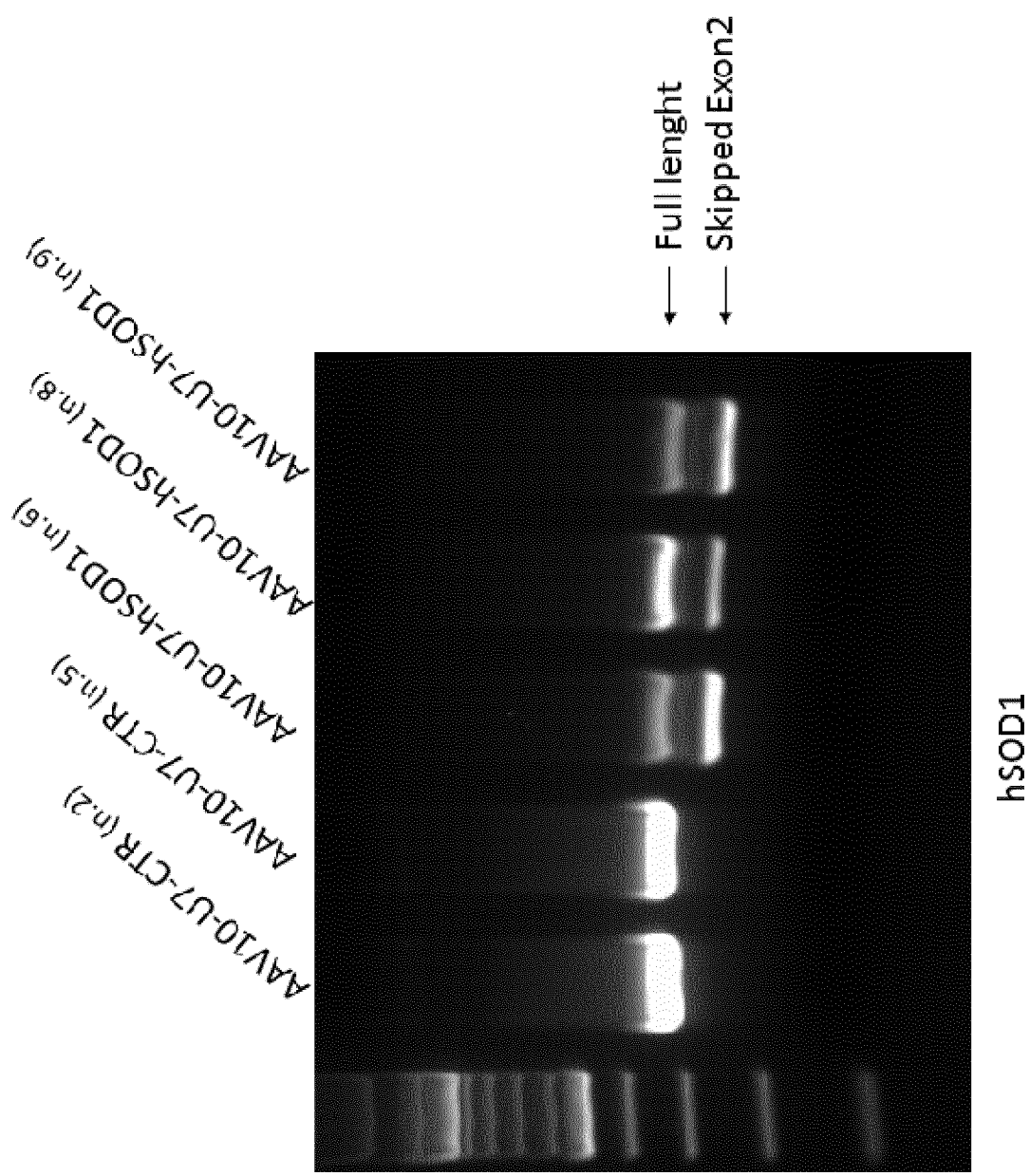

FIG. 5: RT-PCR on spinal cord (SC) extracts from SOD1$^{G93A}$ mice injected directly into the spinal cord (SC) with $4.7 \times 10^{12}$ vg/kg of AAV10-U7-hSOD1 or AAV10-U7-CTR.

Figure 6:
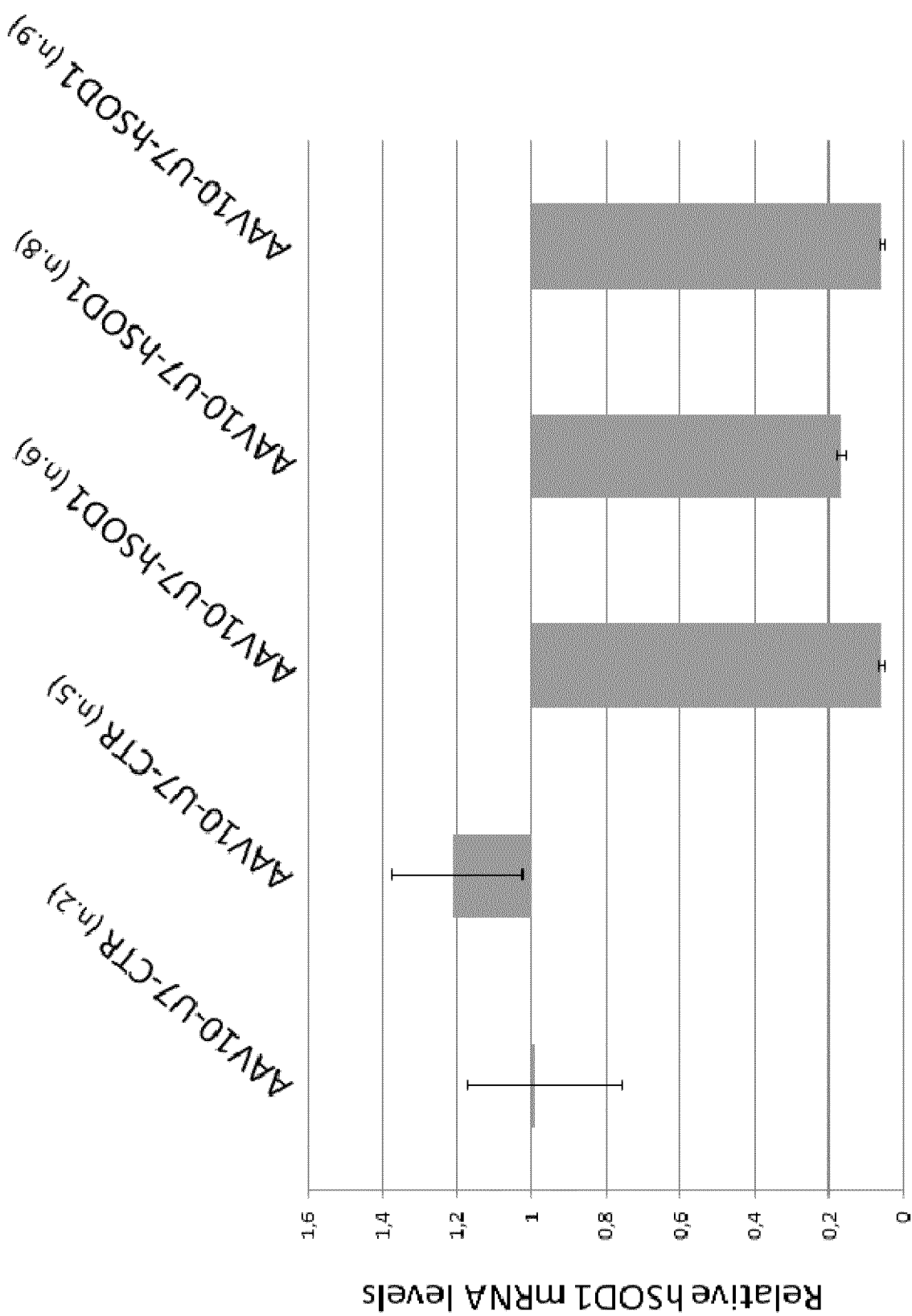

FIG. 6: Q-RT-PCR on full length hSOD1 mRNA in SC extracts from SOD1$^{G93A}$ mice injected directly into the SC. Two mice were injected with $4.7 \times 10^{12}$ vg/kg of AAV10-U7-CTR: n.2 and n.5; three mice were injected with the same dose of AAV10-U7-hSOD1: n.6, n.8 and n.9.

Figure 7:
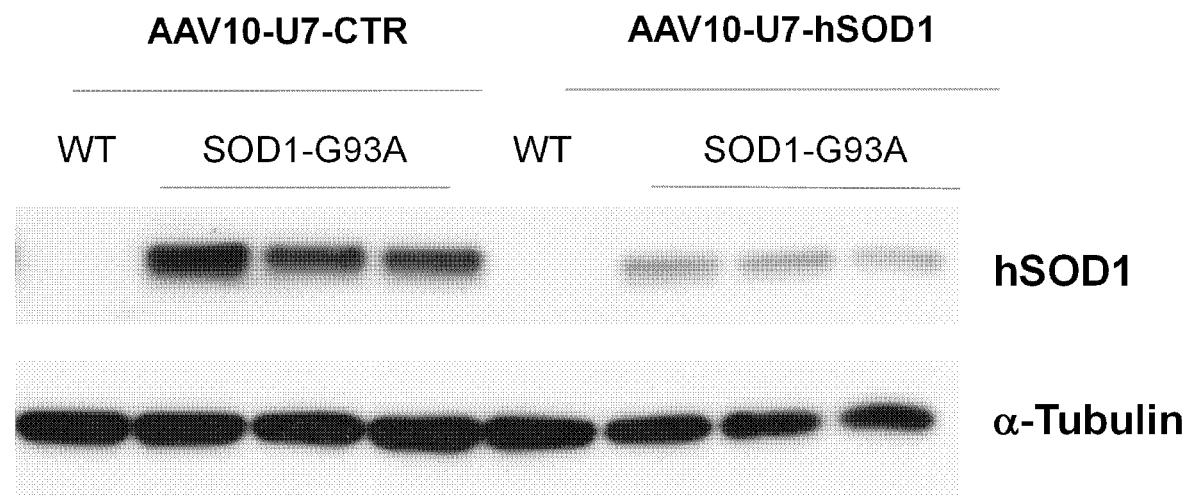
Figure 7:
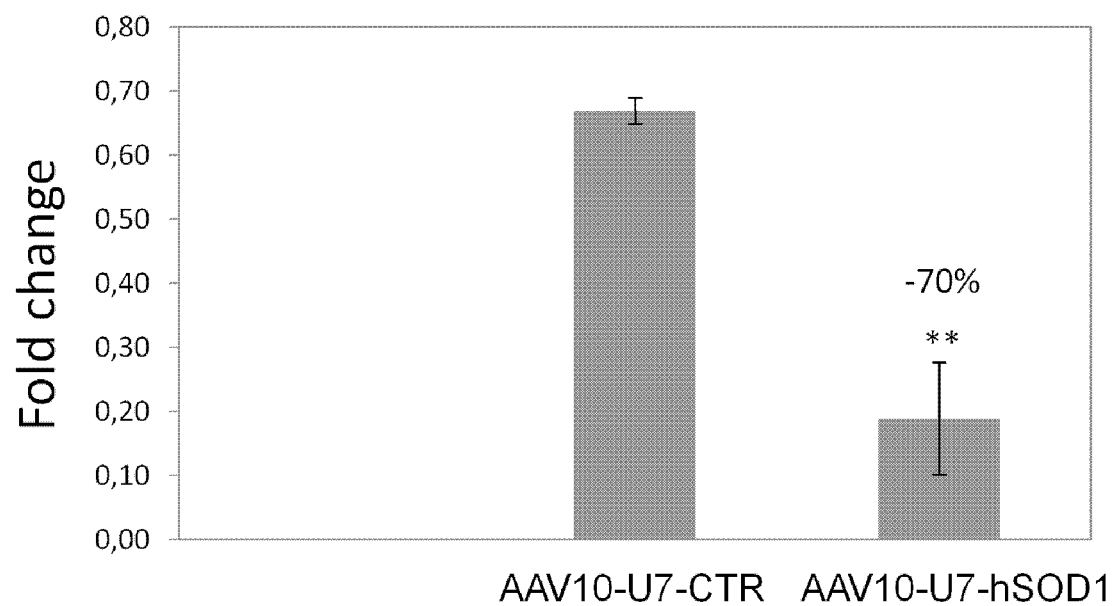

FIG. 7: (a) Western-blot analysis of hSOD1 protein expression in SOD1$^{G93A}$ mice injected into the SC with $4.7 \times 10^{12}$ vg/kg of AAV10-U7-hSOD1 (n=3) and the same dose of AAV10-U7-CTR (n=3). Alpha-Tubulin was used as loading control (b) Densitometric analysis of the protein levels. Data are means+/−SEM (n=3). **P<0.01, determined by Student's t-test compared to AAV10-U7-CTR infected spinal cord.

Figure 8:
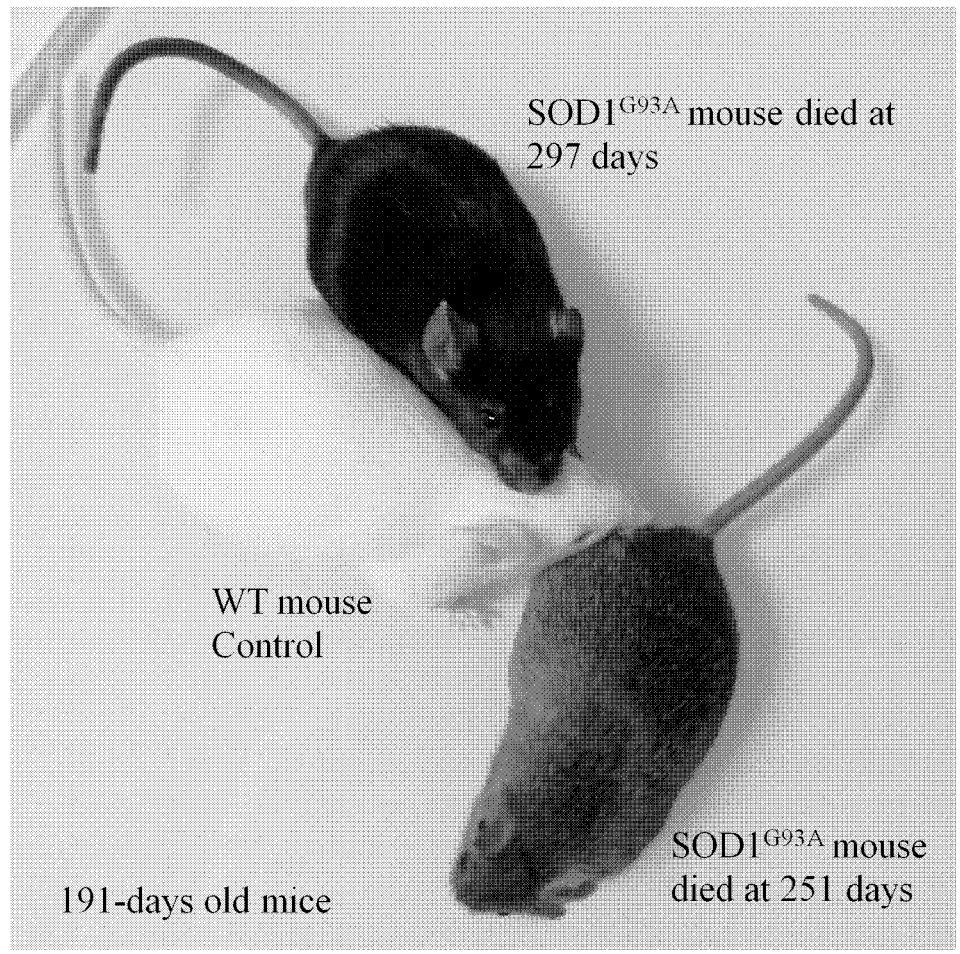

FIG. 8: Representative photograph of SOD1$^{G93A}$ mice injected at birth into the lateral ventricle (ICV) and the temporal vein (IV), with 6×10" vg/kg of AAV10-U7-hSOD1. An age related (191-days old) wild-type (WT) mouse is showed as control.

Figure 9:
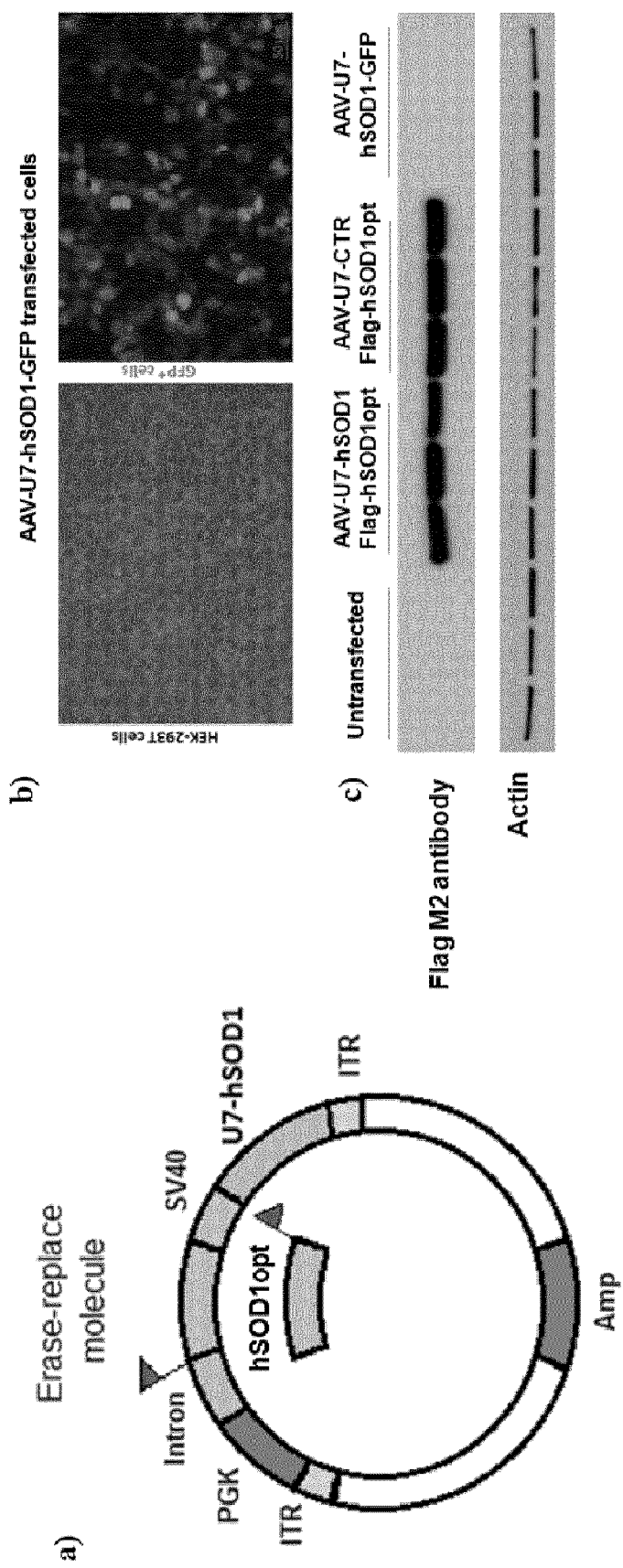

FIG. 9: (a) Schematic representation of an "erase-replace" AAV vector simultaneously expressing the U7-hSOD1 antisense oligonucleotide (under control of the U7 promoter), and the Flag-hSOD1opt or the hSOD1opt-Flag (under control of the PGK promoter): AAV-U7-hSOD1-Flag-hSOD1opt or AAV-U7-hSOD1-hSOD1opt-Flag (b) Representative cultured HEK-293T cells treated by GFP-immunofluorescence 48 hours after transfection with the AAV-U7-hSOD1-GFP control vector (right). The left panel represents a phase contrast image of the cells. (c). Western-blot analysis of the Flag tag in HEK-293 cells 48 hours after transfection with the AAV-U7-CTR-Flag-hSOD1opt, the AAV-U7-hSOD1-Flag-hSOD1opt, or the control AAV-U7-hSOD1-GFP control vector, and in untransfected cells. Actin was used as loading control.

EXAMPLES

Example 1: hSOD1 Silencing and Survival Improvement in ALS Mice

Materials and Methods

Mice Strains (Animals), In Vivo Electroporation and Adeno Associated Virus Vectors (AAV)

Animal care followed the European guidelines for the care and use of experimental animals. High copy SOD1$^{G93A}$ mice, B6SJL-Tg (SOD1*G93A)1Gur/J (JACKSON no. SN 2726) were purchased from Jackson Laboratories (Bar Harbor, Me.).

Cells

HEK-293T cells were cultured in Dulbecco's modified Eagle's medium (DMEM) containing 10% fetal bovine serum (FBS) and 1% penicillin/streptomycin at 37° C. in 5% CO2. 2'-O-methyl phosphorothioate (2'OMePS) AONs were purchased from Eurogentec and re-suspended in H2O RNAse free water at a final concentration of 1 µg/µl. 5 µg of each AON were transfected with Oligofectamine (Invitrogen) following the manufacturer's Instructions. 48 hours after transfection cells were harvested for RNA extraction.

RNA Extraction, Reverse Transcription, RT-PCR and qRT-PCR

Total RNA was extracted from cells or from freshly frozen spinal cords with the RNA extraction kit NucleoSpin RNA II (Macherey-Nagel), as per the manufacturer's protocol. cDNA was synthesized from 1 µg of total RNA using oligo (dT) and random hexamer primers, according to the iScript cDNA Synthesis kit protocol (Biorad). To investigate the presence of exon 2 in the human SOD1 mRNA, RT-PCR analysis was performed from 200 ng of cDNA, using the following primers:

Primer Fw1, matching the human SOD1 exon 1: 5'-CTAGCGAGTTATGGCGAC-3' (SEQ ID NO:5); Primer Rev 4/5, matching the human SOD1 (exon 4-exon 5 boundary): 5'-GCCAATGATGCAATGGTCTC-3' (SEQ ID NO:6).

Taqman Real-time PCR (Q-RT-PCR) was performed using DNA Engine Opticon 2 System (Biorad). 100 ng of cDNA were amplified in 10 µl of Taqman Universal PCR Master Mix 2X (Life technologies), with 1 µl of human SOD1 FAM TaqMan Gene expression assay (Hs00533490 m1, Life technologies) and 1 µl of human GAPDH VIC Taqman Gene expression assay (Hs03929097_g1, Life technologies) or for in vivo analysis mouse Ipo8 (Mm01255158_m1, Life Technologies) as endogenous control. Reactions were incubated 1 min at 60° C., 10 min at 95° C., followed by 39 cycles of 15 min at 95° C. and 1 min at 60° C. The number of hSOD1 copies was calculated using the delta Ct/delta Ct method. Analyses were performed with DNA Engine Opticon® 2 System (Biorad).

Vectors

The DNA sequences corresponding to the two most performing AONs were cloned into the pAAVsc_U7DTex23 (kindly provided by GENETHON, Evry, France), using PCR-mediated mutagenesis, as already described (Goyenvalle et al., 2004). The viral particles, scAAV serotype 10, have been produced using the tri-transfection method, as previously described in Dominguez et al. (Dominguez et al., 2011). Vector titers were determined by Q-RT-PCR on ITRs; titers were expressed as viral genome (vg)/ml.

Injections

For injection into the spinal cord of adult mice, 50-days old mice were used. Mice were anesthetized with an intra-peritoneal injection of a ketamine/xylazine mixture (100 mg/kg Ketamine, 16 mg/kg Xylazine; 0.1 ml per 10 grams of body weight). Injections were performed as reported in Raoul et al. 2005 (Raoul et al., 2005). Total volume of 10 µl (5 µl per site) containing 9.5×10e10 vg (4.7×10e12 vg/Kg) of each vector was injected in each mouse.

For injection into newborn mice, postnatal day 1 pups were utilized. Injections were performed by combining intracerebroventricular (ICV) and intravenous (IV) injections (as described in Barkats, Voit. Patent WO2013190059 (A1)—2013-12-27). Total volume of 80 µl containing 7.6× 10e11 vg (6×10e14 vg/kg) have been injected in each mice. 10 µl of viral solution were injected directly into the lateral ventricles and 70 µl were delivered into the frontotemporal vein.

Western Blot Analysis

Freshly frozen spinal cords were homogenized and protein lysate were prepared using the lysis buffer (150 mM NaCl, 50 mM Tris-HCl, 0.5% sodium deoxycholate, 1% NP40, 1% SDS) supplied with protease inhibitors cocktail (Complete Mini, Roche Diagnostics). Protein extracts were quantified by DC protein assay (BioRad). 30 µg were separated on 12% polyacrylamide gel (Criterion XT 10% bis-Tris, Biorad) and analyzed by Western blot with the following antibodies: anti-α-tubulin (T5168, Sigma Aldrich); anti-human SOD1 (sc-8636, Santa Cruz Biotechnology). Peroxidase-conjugated antisera to mouse and rabbit Igs were purchased from Amersham Pharmacia Biotech. Western blots were developed using the SuperSignal West Dura kit (Thermoscientific). Densitometric analysis was performed using Image J software.

Results

1) AON Design

To induce exon skipping in the human SOD1 gene, we designed RNA-AONs to interfere with the acceptor splice site (SA) or with exon splicing enhancer (ESE) sequences of the human SOD1 pre-mRNA. The human SOD1 gene is composed of 5 exons and we planned to induce the skipping of exon 2. Indeed, skipping exon 2 from the SOD1 pre-mRNA induces a frameshift which produces a truncated cDNA resulting in a premature stop codon (TGA) in exon 4. To optimize skipping of exon 2, we designed AON sequences targeting the SA sequence in intron1 and—since it has been reported that targeting ESE sequences may represent an advantage over SA (Goyenvalle et al., 2004), we also designed AONs targeting exon 2 ESE sequences. ESEs are exon-internal sequences that facilitate splicing by binding Ser-Arg-rich (SR) proteins (Cartegni et al., 2002). To determine these sequences we used the ESEfinder software which predicts binding sites for the four most abundant SR proteins (SF2/ASF, SC35, SRp40, and SRp55). In FIG. 1 are shown potential ESE sequences in exon 2.

Once the putative target sequences were identified, we designed 4 AONs to specifically skip the human SOD1 exon2, following the specific rules published by Aartsma-Rus et al. (Aartsma-Rus et al., 2009). Accordingly, each AON (Table 1) was designed to be 20-nucleotides long, we selected AONs with the highest Tm and we evaluated the free energy of the predicted secondary structure of both AONs and the targeted exon, using the RNAstructure 5.3 software. We also selected a scrambled AONs sequence as negative control (AON-CTR). Sequence control: 5' GCU-CAUUCGCUUUCAUUCUU 3'(SEQ ID NO:7).

2) In Vitro Selection of the AONs

We selected the optimal AONs on the basis of their efficacy to reduce hSOD1 mRNA levels after transfection in HEK-293T cells. To optimize cell transfection, we used chemically modified 2'-O-methyl phosphorothioate (2'OMePS) AONs (Eurogentec), as this modification confers considerable resistance to nuclease and RNase H degradation (Aartsma-Rus et al., 2009). As control we used the scrambled fluorescently (FAM)-labeled AON which has been also used as control of the transfection efficiency in each experiment. After RT-PCR analysis we observed the PCR product corresponding to the human SOD1 mRNA full length (355 bp) in all the samples. In SOD1-AONs transfected cells we observed an additional 258 bp product, corresponding to the skipped Exon 2 form (FIG. 2). After sequencing the PCR products, we confirmed exon2 skipping in the human SOD1-mRNA corresponding to the small 258 bp band (FIG. 3), with the production of a premature stop codon in exon 4. We concluded that the selected AONs were able to induce human SOD1 exon 2 skipping.

To identify the most effective sequence in terms of human SOD1 mRNA levels reduction, the expression of the full length SOD1 mRNA has been quantified by Real Time PCR using the Taqman method. (FIG. 4)

AON1 and AON4 showed the highest efficiency in terms of human SOD1 mRNA reduction (85% and 81% respectively). Accordingly we selected these two AONs to be cloned together in fusion with the U7snRNA sequence into the scAAV backbone. The sequence added to the U7 promoter is: CCCACACCTTCACTGGTCCACCATGCAG-GCCTTCAGTCAG (SEQ ID NO:8)

The complete sequence, U7+ Antisense is:

(SEQ ID NO: 9)
TAACAACATAGGAGCTGTGATTGGCTGTTTTCAGCCAATCAGCACTGACT

CATTTGCATAGCCTTTACAAGCGGTCACAAACTCAAGAAACGAGCGGTTT

TAATAGTCTTTTAGAATATTGTTTATCGAACCGAATAAGGAACTGTGCTT

TGTGATTCACATATCAGTGGAGGGGTGTGGAAATGGCACCTTGATCTCAC

CCTCATCGAAAGTGGAGTTGATGTCCTTCCCTGGCTCGCTACAGACGCAC

TTCCGCAAGCCCACACCTTCACTGGTCCACCATGCAGGCCTTCAGTCAGA

ATTTTTGGAGCAGGTTTTCTGACTTCGGTCGGAAAACCCCTCCCAATTTC

ACTGGTCTACAATGAAAGCAAAACAGTTCTCTTCCCCGCTCCCCGGTGTG

TGAGAGGGGCTTTGATCCTTCTCTGGTTTCCTAGGAAACGCGTATGTG.

3) scAAV10-U7-hSOD1 Production

U7snRNA is normally involved in histone pre-mRNA 3'-end processing, but can be converted into a versatile tool for splicing modulation by a small change in the binding site for Sm/Lsm proteins (U7 smOpt) (Schumperli and Pillai, 2004). The antisense sequence, embedded into a snRNP particle, is therefore protected from degradation and accumulates in the nucleus where splicing occurs. To deliver AONs in SOD1$^{G93A}$ mice, we have used the U7 cassette described by D. Schumperli (Schumperli and Pillai, 2004). It consists of the natural U7-promoter (position −267 to +1), the U7 smOpt snRNA and the downstream sequence down to position 116. This cassette has been placed between the inverted terminal repeats (ITR) of a scAAV backbone and the 18 nt natural sequence complementary to histone pre-mRNAs in U7smOpt has been replaced by the two selected 20-nt AONs sequences (and a control sequence, CTR; described in Pietri-Rouxel, 2009 et al.), and we produced the corresponding viral particles (namely AAV10-U7-CTR and AAV10-U7-hSOD1).

4) In Vivo hSOD1 Exon Skipping in SOD1$^{G93A}$ Mice

To analyze their efficacy in reducing hSOD1 RNA levels, the AAV10-U7-CTL and AAV10-U7-hSOD1 were directly injected into the spinal cord of 50 day-old mice SOD$^{G93A}$ mice (n=3 for the AAV10-U7-hSOD1 and n=2 for the AAV10-U7-CTR. Four weeks post-injection, the spinal cords were removed and SOD mRNAs were analyzed for exon 2 skipping using RT-PCR (FIG. 5). Human SOD1 expression was also assessed by Real time PCR analysis as described in the previous in vitro experiments (FIG. 6). As expected, the Ex2 skipped form was observed only in the spinal cords from the AAV10-U7-hSOD1 injected animals (FIG. 5), with more than 80% reduction of the full length hSOD1 mRNA (FIG. 6).

Similar to the RNA analyses, the effect of Ex2 skipping was further analyzed at the protein level one month after injection of the control and the U7-hSOD1 AAV vectors into the spinal cord of SOD$^{G93A}$ mice (n=3 in each group). The western blot analysis showed a 70% reduction of the hSOD1 protein in the spinal cord of in the 3 AAV10-U7-hSOD1 injected mice compared to the controls (FIG. 7).

The potential therapeutic effect of the AAV10-U7-hSOD1 vector was then investigated in ALS mice by a combined intravenous (IV) and intra-cerebroventricular (ICV) injections in presymptomatic SOD$^{G93A}$ mice in order to achieve both central and systemic hSOD1 reduction (injections at P1; n=4 with 6×10e14 vg/kg of AAV10-U7-hSOD1 and n=3 with the same dose of AAV10-U7-CTR).

The survival of the four AAV10-U7-hSOD1 injected mice was significantly increased compared to control injected mice, the mean survival being of 260 days, versus 128 days in the non-injected controls (FIG. 7). This survival extent (up to 134%) is the highest reported to date in SOD1-linked ALS mice, suggesting the originality and superiority of our molecular approach.

Conclusion

This study is a translational project aimed at identifying strongly effective gene therapy treatments for familial ALS. Co-delivery of scAAV10 in the bloodstream and the CNS (Co-IV/ICV) is a powerful approach for widespread spinal cord and whole body gene delivery. The combination of Co-IV/ICV AAV10 gene transfer with the efficient exon-skipping strategy allows a strong silencing of hSOD1 and mediates the highest survival extent reported to date in ALS rodents. As a comparison, the Cleveland/ISIS clinical trial using brain infusion of ASOs is based on 9.1% extension in rat survival (Smith et al., 2006), and 38% increased survival has been recently published by the Kaspar's team using AAV9-shRNA (Foust et al., 2013).

These preliminary results opens new realistic venues for even further increase in ALS mouse survival, and could be directly translated to clinical development in the next future.

The results presented in example 1 showed that AAV10-U7-hSOD1 injection provided a considerable therapeutic benefit in SOD1$^{G93A}$ mice by silencing hSOD1.

Example 2: "Erase-Replace" Strategy

The therapeutic benefit of AAV10-U7-hSOD1 delivery could be improved by further expression of the wild-type hSOD1 protein. Indeed, AAV10-U7-hSOD1 delivery, which does not target specifically the mutated form of the human SOD1 mRNA, could also induce silencing of the endogenous wild-type SOD1 protein, thereby triggering potential side-effects. Silencing of the endogenous wild-type SOD1 by AAV10-U7-hSOD1 could be compensated by introducing into this vector a wild-type SOD1 sequence comprising "silent" mutations in order to avoid exon skipping.

The following section presents data in this regard.

Materials and Methods

Vectors

The DNA sequences encoding for the hSOD1opt with the flag tag at the N terminal or the C terminal, were synthetized by Gene Art (Life technologies) and initially cloned by enzymatic digestion into an empty pAAV vector available in our laboratory carrying the phophoglycerate kinase (PGK) promoter, a chimeric 0 globin intron, a unique restriction site Nhe I, and the termination signal of the Simian Virus 40 (SV40). The cassette containing the hSOD1opt under the control of the PGK promoter was cloned by PCR into the pAAV-U7-SOD1 vector or the pAAV-U7-CTR, before the U7 promoter and in two directions. With the same method the PGK-GFP, amplified from a plasmid available in the laboratory, was inserted in each pAAV-U7, as control.

Vector nomenclature is provided in the following table:

| Vector name | Description |
|---|---|
| Vectors for erase/replace strategy | |
| pAAV-U7-hSOD1-Flag-hSOD1opt | AAV-U7-hSDO1 co-expressing the PGK-hSOD1opt with Flag at the N-Terminal end |
| pAAV-U7-hSOD1-hSOD1opt-Flag | AAV-U7-hSOD1 co-expressing the PGK-hSOD1opt with Flag at the C-Terminal end |
| Control vectors | |
| pAAV-U7-CTR-Flag-hSOD1opt | AAV-U7-CTR co-expressing the PGK-hSOD1opt with Flag at the N-Terminal vector |
| pAAV-U7-CTR-hSOD1opt-Flag | AAV-U7-CTR co-expressingthe PGK-hSOD1opt with Flag at the C-Terminal |
| pAAV-U7-hSOD1-GFP | AAV-U7-hSDO1 co-expressing the PGK-GFP |
| pAAV-U7-hSOD1-GFP | AAV-U7-CTR co-expressing the PGK-GFP |

Cells

2 µg of each plasmids were transfected with the Lipofectamine and Plus Reagent (Life technologies) in OPTIMEM (Life technologies) medium without FBS (according to manufacturer's instructions). After 3 hours at 37° C. in 5% CO2, transfection was stopped with the addition of DMEM with 10% FBS.

Western Blot Analysis

Cells were harvested 48 h after transfection; protein lysates were prepared as described in example 1. Western blot was performed with the following antibodies: anti-Flag M2 (Sigma) and anti-actin (Sigma). Peroxidase-conjugated antisera to mouse and rabbit Igs were purchased from Amersham Pharmacia Biotech. Western blots were developed using the SuperSignal West Dura kit (Thermoscientific).

Results

To obtain both the suppression of the toxic mutated hSOD1 and the expression of a functional hSOD1 protein, we conceived an "erase-replace" strategy, in which the silencing pAAV-U7-hSOD1 vector was provided with an exogenous hSOD1 cDNA for wild-type SOD1 expression. The wild-type hSOD1-coding sequence (hSOD1 opt) was designed to carry a maximum number of mismatches with the antisense sequence in order to be refractory to the U7-antisense action (GeneArt, Life technologies). To allow the identification of the exogenous hSOD1protein, a Flag-tag peptide was fused to the cDNA. Since the C- or N-terminal position of the Flag could have effects on hSOD1opt expression and/or function this one was added either at the N-terminal (Flag-hSOD1opt) or at the C-terminal end (hSOD1opt-Flag) of the protein. The sequence was placed under the control of the phosphoglycerate kinase (PGK) promoter, in the same direction as the U7 promoter or in the opposite direction. The final therapeutic AAV vectors, AAV-U7-hSOD1-Flag-hSOD1opt and AAV-U7-hSOD1-Flag are shown in FIG. 9. A sequence encoding the green fluorescent protein (GFP), placed under the control of the PGK promoter, was also inserted into the pAAV-U7 vectors as control (pAAV-U7-hSOD1-GFP).

To investigate whether these new AAV-U7 silencing vectors could simultaneously induce hSOD1 expression, human embryonic kidney (HEK-293T) cells were first transfected with pAAV-U7-hSOD1-GFP and GFP expression was investigated 48 hours later by live imaging with an epifluorescence microscope (FIG. 9b). The GFP fluorescence results indicated that the two vectors carrying both the U7 molecule (U7-SOD1 or U7-CTR) and the GFP expression cassette were efficient for protein production. Furthermore, the expression of the hSOD1opt, was assessed by western blot analysis for the flag tag in cell lysates 48 h after transfection (FIG. 9c), revealing the efficient synthesis of the tagged hSOD1opt protein.

Collectively, these data showed that AONs inducing exon-skipping in a mutated form of the hSOD1 mRNA may be designed to strongly decrease hSOD1 protein levels, and that concomitant expression of exogenous hSOD1 protein can be carried out using an optimized coding sequence.

REFERENCES

Aartsma-Rus, A., van Vliet, L., Hirschi, M., Janson, A. A., Heemskerk, H., de Winter, C. L., de Kimpe, S., van Deutekom, J. C., t Hoen, P. A., and van Ommen, G. J. (2009). Guidelines for antisense oligonucleotide design and insight into splice-modulating mechanisms. Mol Ther 17, 548-553.

Betts, C., Saleh, A. F., Arzumanov, A. A., Hammond, S. M., Godfrey, C., Coursindel, T., Gait, M. J., and Wood, M. J. (2012). Pip6-PMO, A New Generation of Peptide-oligonucleotide Conjugates With Improved Cardiac Exon Skipping Activity for DMD Treatment. Molecular therapy Nucleic acids 1, e38.

Boudreau, R. L., Rodriguez-Lebron, E., and Davidson, B. L. (2011). RNAi medicine for the brain: progresses and challenges. Hum Mol Genet 20, R21-27.

Cartegni, L., Chew, S. L., and Krainer, A. R. (2002). Listening to silence and understanding nonsense: exonic mutations that affect splicing. Nat Rev Genet 3, 285-298.

Cazzella, V., Martone, J., Pinnaro, C., Santini, T., Twayana, S. S., Sthandier, O., D'Amico, A., Ricotti, V., Bertini, E., Muntoni, F., et al. (2012). Exon 45 skipping through U1-snRNA antisense molecules recovers the Dys-nNOS pathway and muscle differentiation in human DMD myoblasts. Mol Ther 20, 2134-2142.

Chan, J. H., Lim, S., and Wong, W. S. (2006). Antisense oligonucleotides: from design to therapeutic application. Clinical and experimental pharmacology & physiology 33, 533-540.

Crooke, S. T. (2004). Antisense strategies. Current molecular medicine 4, 465-487.

De Angelis, F. G., Sthandier, O., Berarducci, B., Toso, S., Galluzzi, G., Ricci, E., Cossu, G., and Bozzoni, I. (2002). Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci USA 99, 9456-9461.

Dominguez, E., Marais, T., Chatauret, N., Benkhelifa-Ziyyat, S., Duque, S., Ravassard, P., Carcenac, R., Astord, S., Pereira de Moura, A., Voit, T., et al. (2011). Intravenous scAAV9 delivery of a codon-optimized SMN1 sequence rescues SMA mice. Hum Mol Genet 20, 681-693.

Dorn, G., Patel, S., Wotherspoon, G., Hemmings-Mieszczak, M., Barclay, J., Natt, F. J., Martin, P., Bevan, S., Fox, A., Ganju, P., et al. (2004). siRNA relieves chronic neuropathic pain. Nucleic Acids Res 32, e49.

Duque, S., Joussemet, B., Riviere, C., Marais, T., Dubreil, L., Douar, A. M., Fyfe, J., Moullier, P., Colle, M. A., and Barkats, M. (2009). Intravenous administration of self-complementary AAV9 enables transgene delivery to adult motor neurons. Mol Ther 17, 1187-1196.

Foust, K. D., Salazar, D. L., Likhite, S., Ferraiuolo, L., Ditsworth, D., Ilieva, H., Meyer, K., Schmelzer, L., Braun, L., Cleveland, D. W., et al. (2013). Therapeutic AAV9-mediated Suppression of Mutant SOD1 Slows Disease Progression and Extends Survival in Models of Inherited ALS. Mol Ther.

Gao, G., Vandenberghe, L. H., Alvira, M. R., Lu, Y., Calcedo, R., Zhou, X., and Wilson, J. M. (2004). Clades of Adeno-associated viruses are widely disseminated in human tissues. J Virol 78, 6381-6388.

Gao, G. P., Alvira, M. R., Wang, L., Calcedo, R., Johnston, J., and Wilson, J. M. (2002). Novel adeno-associated viruses from rhesus monkeys as vectors for human gene therapy. Proc Natl Acad Sci USA 99, 11854-11859.

Goyenvalle, A., Vulin, A., Fougerousse, F., Leturcq, F., Kaplan, J. C., Garcia, L., and Danos, O. (2004). Rescue of dystrophic muscle through U7 snRNA-mediated exon skipping. Science 306, 1796-1799.

Gurney, M. E., Pu, H., Chiu, A. Y., Dal Canto, M. C., Polchow, C. Y., Alexander, D. D., Caliendo, J., Hentati, A., Kwon, Y. W., Deng, H. X., et al. (1994). Motor neuron degeneration in mice that express a human Cu,Zn superoxide dismutase mutation. Science 264, 1772-1775.

Hu, C., Busuttil, R. W., and Lipshutz, G. S. (2010). RH10 provides superior transgene expression in mice when compared with natural AAV serotypes for neonatal gene therapy. The journal of gene medicine 12, 766-778.

Ilieva, H., Polymenidou, M., and Cleveland, D. W. (2009). Non-cell autonomous toxicity in neurodegenerative disorders: ALS and beyond. J Cell Biol187, 761-772.

Kumar, P., Wu, H., McBride, J. L., Jung, K. E., Kim, M. H., Davidson, B. L., Lee, S. K., Shankar, P., and Manjunath, N. (2007). Transvascular delivery of small interfering RNA to the central nervous system. Nature 448, 39-43.

Lundberg, M., Wikstrom, S., and Johansson, M. (2003). Cell surface adherence and endocytosis of protein transduction domains. Mol Ther 8, 143-150.

Malhotra, M., Tomaro-Duchesneau, C., Saha, S., Kahouli, I., and Prakash, S. (2013). Development and characterization of chitosan-PEG-TAT nanoparticles for the intracellular delivery of siRNA. International journal of nanomedicine 8, 2041-2052.

McCarty, D. M., Monahan, P. E., and Samulski, R. J. (2001). Self-complementary recombinant adeno-associated virus (scAAV) vectors promote efficient transduction independently of DNA synthesis. Gene Ther 8, 1248-1254.

Miller, T. M., Pestronk, A., David, W., Rothstein, J., Simpson, E., Appel, S. H., Andres, P. L., Mahoney, K., Allred, P., Alexander, K., et al. (2013). An antisense oligonucleotide against SOD1 delivered intrathecally for patients with SOD1 familial amyotrophic lateral sclerosis: a phase 1, randomised, first-in-man study. Lancet neurology 12, 435-442.

Pietri-Rouxel F., Gentil C, Vassilopoulos S, Baas D, Mouisel E, Ferry A, Vignaud A, Hour& C, Marty I, Schaeffer L, Voit T, Garcia L. et al. (2009) DHPR alphal S subunit controls skeletal muscle mass and morphogenesis. EMBO J 29, 643-654.

Ralph, G. S., Radcliffe, P. A., Day, D. M., Carthy, J. M., Leroux, M. A., Lee, D. C., Wong, L. F., Bilsland, L. G., Greensmith, L., Kingsman, S. M., et al. (2005). Silencing mutant SOD1 using RNAi protects against neurodegeneration and extends survival in an ALS model. Nat Med 11, 429-433.

Raoul, C., Abbas-Terki, T., Bensadoun, J. C., Guillot, S., Haase, G., Szulc, J., Henderson, C. E., and Aebischer, P. (2005). Lentiviral-mediated silencing of SOD1 through RNA interference retards disease onset and progression in a mouse model of ALS. Nat Med 11, 423-428.

Reed, R., and Maniatis, T. (1988). The role of the mammalian branchpoint sequence in pre-mRNA splicing. Genes & development 2, 1268-1276.

Rosen, D. R., Siddique, T., Patterson, D., Figlewicz, D. A., Sapp, P., Hentati, A., Donaldson, D., Goto, J., O'Regan, J. P., Deng, H. X., et al. (1993). Mutations in Cu/Zn superoxide dismutase gene are associated with familial amyotrophic lateral sclerosis. Nature 362, 59-62.

Schumperli, D., and Pillai, R. S. (2004). The special Sm core structure of the U7 snRNP: far-reaching significance of a small nuclear ribonucleoprotein. Cell Mol Life Sci 61, 2560-2570.

Smith, R. A., Miller, T. M., Yamanaka, K., Monia, B. P., Condon, T. P., Hung, G., Lobsiger, C. S., Ward, C. M., McAlonis-Downes, M., Wei, H., et al. (2006). Antisense oligonucleotide therapy for neurodegenerative disease. J Clin Invest 116, 2290-2296.

Wang, H., Yang, B., Qiu, L., Yang, C., Kramer, J., Su, Q., Guo, Y., Brown, R. H., Jr., Gao, G., and Xu, Z. (2013). Widespread spinal cord transduction by intrathecal injection of rAAV delivers efficacious RNAi therapy for amyotrophic lateral sclerosis. Hum Mol Genet.

Ward, A. J., Norrbom, M., Chun, S., Bennett, C. F., and Rigo, F. (2014). Nonsense-mediated decay as a terminating mechanism for antisense oligonucleotides. Nucleic Acids Res 42, 5871-5879.

Yamada, T., Das Gupta, T. K., and Beattie, C. W. (2013). p 28, an anionic cell-penetrating peptide, increases the activity of wild type and mutated p53 without altering its conformation. Molecular pharmaceutics 10, 3375-3383.

Yang, B., Li, S., Wang, H., Guo, Y., Gessler, D. J., Cao, C., Su, Q., Kramer, J., Zhong, L., Seher Ahmed, S., et al. (2014). Global CNS Transduction of Adult Mice by Intravenously Delivered rAAVrh.8 and rAAVrh.10 and Nonhuman Primates by rAAVrh.10. Mol Ther.

Zhang, H., Yang, B., Mu, X., Ahmed, S. S., Su, Q., He, R., Wang, H., Mueller, C., Sena-Esteves, M., Brown, R., et al. (2011). Several rAAV vectors efficiently cross the blood-brain barrier and transduce neurons and astrocytes in the neonatal mouse central nervous system. Mol Ther 19, 1440-1448.

The invention claimed is:

1. An antisense oligonucleotide of 20 to 30 nucleotides in length targeting a human SOD1 pre-mRNA, wherein said antisense oligonucleotide comprises SEQ ID NO:1.

2. A nucleic acid molecule comprising: (i) a nucleic acid sequence of SEQ ID NO:1 and (ii) a nucleic acid sequence of SEQ ID NO:4.

3. An antisense oligonucleotide of 20 to 30 nucleotides in length targeting a human SOD1 pre-mRNA, wherein said antisense oligonucleotide comprises SEQ ID NO: 1 and wherein said antisense oligonucleotide is modified with a small nuclear RNA such as the U7 small nuclear RNA.

4. A vector comprising a nucleic acid that encodes an antisense oligonucleotide of 20 to 30 nucleotides in length targeting a human SOD1 pre-mRNA, wherein said antisense oligonucleotide comprises SEQ ID NO: 1.

5. The vector according to claim 4, which is a viral vector.

6. The vector according to claim 5, wherein said viral vector is an AAV vector, in particular an AAV9 or AAV10 vector.

7. A vector encoding at least one antisense oligonucleotide targeting a human SOD1 pre-mRNA, wherein said antisense oligonucleotide induces exon-skipping in said pre-mRNA, wherein said vector further comprises an expression cassette containing a nucleotide sequence encoding a human SOD1 protein, wherein said nucleotide sequence comprises SEQ ID NO:11 or SEQ ID NO:12, wherein the antisense oligonucleotide cannot induce exon-skipping in the pre-mRNA encoded by said nucleotide sequence.

8. A method for treating amyotrophic lateral sclerosis, comprising administering to a subject in need thereof an antisense oligonucleotide of 20 to 30 nucleotides in length targeting a human SOD1 pre-mRNA, wherein said antisense oligonucleotide comprises SEQ ID NO: 1.

9. The method of claim 8, wherein said antisense oligonucleotide is administered via the intravenous or intracerebroventricular routes.

10. A nucleic acid sequence comprising the sequence of SEQ ID NO:11 or 12.

11. An expression cassette comprising the nucleic acid sequence of claim 10.

12. A vector comprising the nucleic acid sequence of claim 10.

13. The vector according to claim 12, wherein said vector is a plasmid or a viral vector.

14. A host cell transformed with a vector according to claim 13.

15. The host cell according to claim 14, said cell being an eukaryotic or prokaryotic cell.

16. The host cell according to claim 14, being a mammalian, human or non-human cell.

17. The host cell according to claim 16, with the proviso that when the cell is a human cell, said cell is not a human embryonic stem cell.

18. The vector according to claim 7, wherein the antisense oligonucleotide comprises SEQ ID NO:1 or SEQ ID NO:4.

19. The vector according to claim 7, wherein the vector encodes an antisense oligonucleotide comprising SEQ ID NO:1 and an antisense oligonucleotide comprising SEQ ID NO:4.

20. A method for treating amyotrophic lateral sclerosis, comprising administering to a subject in need thereof the vector according to claim 4.

21. The method of claim 20, wherein said vector is administered via the intravenous or intracerebroventricular routes.

22. A method for treating amyotrophic lateral sclerosis, comprising administering to a subject in need thereof the vector according to claim 7.

23. The method of claim 22, wherein said vector is administered via the intravenous or intracerebroventricular routes.

24. The nucleic acid molecule according to claim 2, wherein said nucleic acid sequence is modified with a small nuclear RNA such as the U7 small nuclear RNA.

25. A method for treating amyotrophic lateral sclerosis, comprising administering to a subject in need thereof the nucleic acid molecule according to claim 2.

26. The method of claim 25, wherein said nucleic acid molecule is administered via the intravenous or intracerebroventricular routes.

27. A vector comprising the nucleic acid molecule according to claim 2.

28. The vector according to claim 27, which is a viral vector.

29. The vector according to claim 28, wherein said viral vector is an AAV vector, in particular an AAV9 or AAV10 vector.

30. A method for treating amyotrophic lateral sclerosis, comprising administering to a subject in need thereof the vector according to claim 27.

31. The method of claim 30, wherein said vector is administered via the intravenous or intracerebroventricular routes.

32. A composition comprising an antisense oligonucleotide comprising SEQ ID NO:1 and an antisense oligonucleotide comprising SEQ ID NO:4.

33. A method for treating amyotrophic lateral sclerosis, comprising administering to a subject in need thereof the composition according to claim 32.

34. The method of claim 33, wherein said composition is administered via the intravenous or intracerebroventricular routes.

* * * * *